Figure 2:
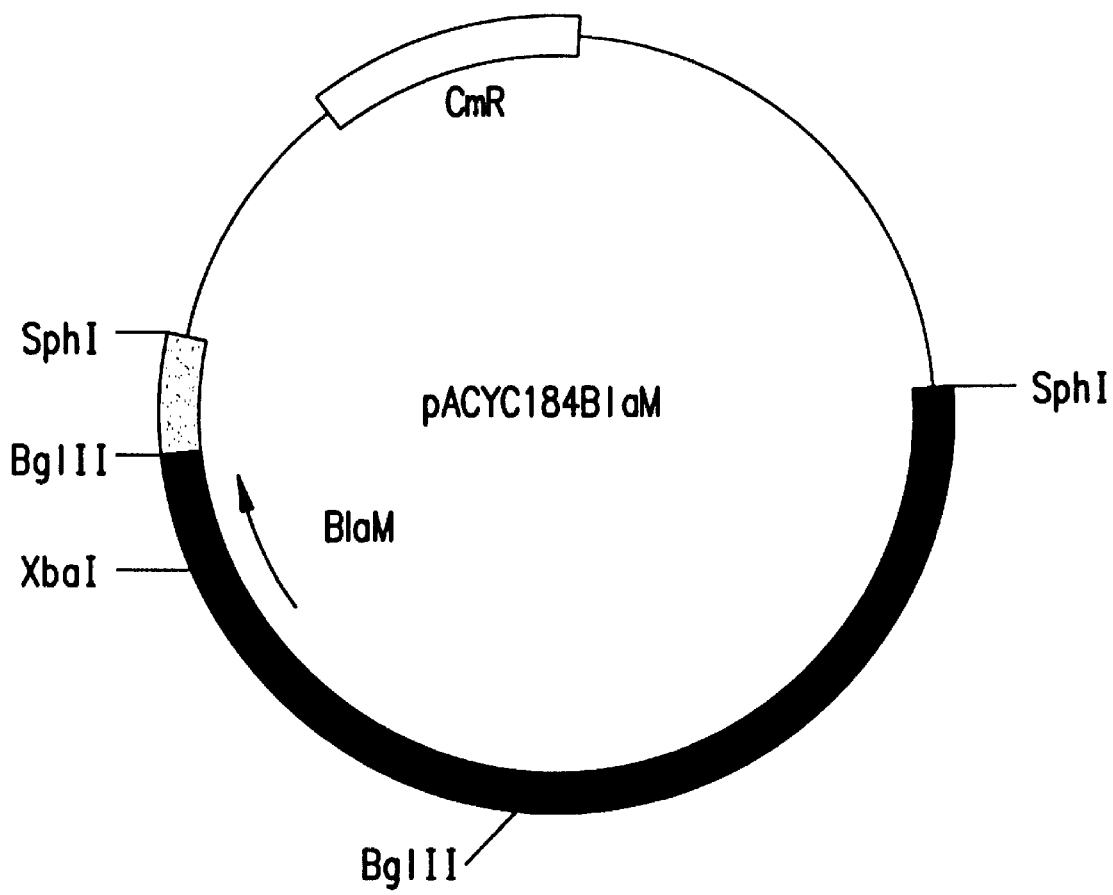

United States Patent [19]
Gicquel et al.

[11] Patent Number: 5,830,457
[45] Date of Patent: Nov. 3, 1998

[54] RECOMBINANT BETA-LACTAMASE, USABLE AS CARRIER MOLECULE IN IMMUNOGENIC COMPOSITIONS

[75] Inventors: Brigitte Gicquel; Juliano Timm, both of Paris, France; Joaquim Trias, San Mateo, Calif.; Colette Duez, Angleur, Belgium; Maria-Grazia Perilli, L'Aquilie, Italy; Jean Dusart; Jean-Marie Frere, both of Nandrin, Belgium

[73] Assignee: Institut Pasteur, Paris Cedex, France

[21] Appl. No.: 284,465

[22] PCT Filed: Feb. 12, 1993

[86] PCT No.: PCT/FR93/00151

§ 371 Date: Nov. 14, 1994

§ 102(e) Date: Nov. 14, 1994

[87] PCT Pub. No.: WO93/17113

PCT Pub. Date: Sep. 2, 1993

[30] Foreign Application Priority Data

Feb. 14, 1992 [FR] France ................................... 92 01713

[51] Int. Cl.⁶ .............................. C07H 21/04; C12N 1/21; C12N 1/19; C12N 15/63

[52] U.S. Cl. ........................ 424/93.2; 536/23.2; 536/23.4; 435/252.3; 435/254.11; 435/254.3; 435/320.1; 530/350

[58] Field of Search ................................... 536/23.2, 23.4; 435/240.2, 252.3, 320.1, 254.11, 254.3; 424/93.2; 530/350

[56] References Cited

FOREIGN PATENT DOCUMENTS 0 012 494  6/1980  European Pat. Off. .

*Primary Examiner*—Robert A. Wax
*Assistant Examiner*—Kawai Lau
*Attorney, Agent, or Firm*—Oblon, Spivak, McClelland, Maier & Neustadt, P.C.

[57] ABSTRACT

The present invention relates to a nucleotide sequence characterized in that it is selected amongst the following nucleotide sequences: the sequence of the gene coding for a B-lactamase, or any part of said gene, particularly the sequence between nucleotides 1 and 394 containing the signals for expression of the gene, or the coding sequence comprising nucleotides 395 to 1274, or any sequence hybridizing under stringent conditions with the above sequence. Utilization of B-lactamase as a carrier protein for carrying heterolog epitopes for the preparation of vaccine compositions is also disclosed.

40 Claims, 20 Drawing Sheets

```
SA: VHPSTSRSPSRRT

MF:  MTGLSRRNVLIGSLVAAAAVGAGVGGAAPAFAAPIDDQLAELERRDNVLI
SA:  ILTATAGAALAAATLVPGTAHASSGGRGHGSGSVSDAERRLAGLERASGARL
AU:               MKKLIFLIVIALVLSACNSNSSHAKE.LNDLEKKYNAHI
                                                      α1        β1

MF: GLYAANLQSGRRITHRPDEMFAMCSTFKGYVGCGVLQMAEH.GEISLDNRVF
SA: GVYAYDTGSGRTVAYRADELFPMCSVFKTLSSAAVLRDLDRNGEF.LSRRIL
AU: GVYALDTKSGKEVKFNSDKRFAYASTSKAINSAILLEQVPYNK...LNKKVH
         β2                    α2

MF: VDADALVPN....SPVTETRAGA...EMILAELCQAALQRSDNTAANLLLKT
SA: YTQDD.VEQADGAGPETGKPQNLANAQLTVEELCEVSITASDNCAANLMLRE
AU: INKDDIVAY....SPILEKYVGK...DITLKALIEASMTYSDNTANNKIIKE
              α3              α4            α5

MF: IGGPAAVTAFARSVGDERTRLDRWEVELNSAIPGDPRDTSTPAGLAVGYRAI
SA: LGGPAAVTRFVRSLGDRVTRLDRWEPELNSAEPGRVTDTTSPRAITRTYGRL
AU: IGGIKKVKQRLKELGDKVTNPVRYEIELNYYSPKSKKDTSTPAAFGKTLNKI
        α6              α7              α8

MF: LAGDALSPPQRA...CWKTGCGPIEPRACVPGPEGWTTADKTGSG.DYGSTN
SA: VLGDALNPRDRALLTSWLLANTTSGDRFRAGLPDDWTLGDKTGAG.RYG.TN
AU: IANGKLSKENKKFLLDLMLNNKSGDTLIKDGVPKDYKVADKSGQAITYASEN
          α9              α10          β3        β4

MF: DAGIAFGPDGQRLLLVMMTRSQAHDPKAENLRPLIGELTALVLPSLL
SA: DAGVTWP.PGRAPIVLTVLTAKTEQDAARDDGLVADAARVLAETLG
AU: DVAFVYPKGQSEPIVLLVIFTNKDNKSDKPNDK.LISETAKSVMKEE
       β5             α11
```

```
GCCCGATCG ATGATCAGCT GGCGGAACTG GAGCGTCGGG ACAACGTCCT GATCGGCTTG   60
TACGCAGCCA ATCTGCAGTC TGGGCGGAGG ATCACGCACC GTCTCGACGA GATGTTCGCG  120
ATGTGCTCGA CGTTCAAGGG TTATG                                        145
```

FIG.1

```
CTCTGTCGTG  TATGCGGATG  TCAGCCGGAA  CGTTCGACAA  AGTGGTGCGG  GTGACCACCG   60
AAGTTTTGGA  AGGTGTTGCC  AGAAGACGGG  TCACCGCCGA  CGAATGCCGG  ATCCGCAAAG  120
GCTCGTTGCG  CGGTGGGCTG  GTGCTCGGCC  TGGAGGATTC  CGGATCACGT  AAGCACGGA   180
TCGGCCGTAG  CGAGCTCAAT  TACGGTGAGC  ACGGACCAT   CGACCACACG  CTGCTGGCCC  240
AGATCGAAGC  AGTCACTCTA  GAAGAGGTCA  ACGCCGTCGC  TCACCAGTTC  GTGTCGCGGG  300
ACTACGGTGC  CGCCGTACTC  GGTCCCTATA  GTTCGAAAAA  GCGCTGCCAC  AACAGCTTCA  360
AACTATCGCC  GGCTGACCCG  CTACACTGGG  TCCA  ATG   ACC GGA CTA  TCG CGA    412
                                      Met   Thr Gly Leu  Ser Arg
                                                              5

CGC AAC GTT CTG ATC GGT TCG CTC GTG GCG GCA GCT GCC GTC GGT           457
Arg Asn Val Leu Ile Gly Ser Leu Val Ala Ala Ala Ala Val Gly
                 10                  15                  20

GCC GTC GGT GGC GCC GGT GCA CCG GCA TTC GCG GCA CCG ATC GAT           502
Ala Val Gly Gly Ala Gly Ala Pro Ala Phe Ala Ala Pro Ile Asp
                 25                  30                  35

GAC CAG CTG GAA CTG GAG CGT CGG GAC AAC GTC CTG ATC GGC               547
Asp Gln Leu Glu Leu Glu Arg Arg Asp Asn Val Leu Ile Gly
                 40                  45                  50

TTG TAC GCA GCC AAT CTG CAG TCT GGG CGG ATC ACG CAC CGT               592
Leu Tyr Ala Ala Asn Leu Gln Ser Gly Arg Ile Thr His Arg
                 55                  60                  70

CCC GAC GAG ATG TTC GCG ATG TGC TCG ACG TTC AAG GGC TAC GTC           632
Pro Asp Glu Met Phe Ala Met Cys Ser Thr Phe Lys Gly Tyr Val
                 75                  80                  85

GGC TGC GGG GTG CAG CTG ATG GCC GAG CAC GGC GAG ATC TCA CTG           677
Gly Cys Gly Val Gln Leu Met Ala Glu His Gly Glu Ile Ser Leu
                 90                  95                 100

GAC AAC CGG GTC TTC GTC GAT GCG GAT GCG CTC GTG CCG AAC TCA           722
Asp Asn Arg Val Phe Val Asp Ala Asp Ala Leu Val Pro Asn Ser
            105                 110                 115

FIG. 4A
```

```
CCC GTC ACC GAG ACA CGT GCC GGT GCC GAG ATG ACG TTG GCC GAG         767
Pro Val Thr Glu Thr Arg Ala Gly Ala Glu Met Thr Leu Ala Glu
            120                 125                 130

CTG TGC CAG GCG CTG CAG CGC CTG CAG CGC AGT GAC AAC ACC GCG GCG AAC 812
Leu Cys Gln Ala Leu Gln Arg Ser Aap Asn Thr Ala Ala Asn
            135                 140                 145

TTG CTG CTG AAG ACC ATT GGC GGG CCT GCG GCT GTC ACC GCC TTC         857
Leu Leu Leu Lys Thr Ile Gly Gly Pro Ala Ala Val Thr Ala Phe
            150                 155                 160

GCC CGC AGC GTC GGC GAT GAG CGC ACC CGC CTG GAC CGG TGG GAG         902
Ala Arg Ser Val Gly Asp Glu Arg Thr Arg Leu Asp Arg Trp Glu
            165                 170                 175

GTA GAG CTG AAC TCC GCG ATA CCC GAC CCG AGG GAC AGC         947
Val Glu Leu Asn Ser Ala Ile Pro Gly Asp Pro Arg Asp Thr Ser
            180                 185                 190

ACG CCG GCG GGC CTG GCG GTC GGA TAC CGC GCG ATT CTG GCC GGT         992
Thr Pro Ala Gly Leu Ala Val Gly Tyr Arg Ala Ile Leu Ala Gly
            195                 200                 205

GAC GCA CTG AGC CCG CCG CAG CGC GCC TGT TGG AAG ACT GGA TGC         1037
Asp Ala Leu Ser Pro Pro Gln Arg Ala Cys Trp Lys Thr Gly Cys
            210                 215                 220

GGG CCA ATC GAG CCT CGA GCA TGC GTG CCG GGC TTC CCG GAG GGC         1082
Gly Pro rle Glu Pro Arg Ala Cys Val Pro Gly Phe Pro Glu Gly
            225                 230                 235
```

FIG. 4B

```
TGG ACC ACC GCG GAC AAA ACC GGC AGC GGC GAT TAC GGC AGC ACC           1127
Trp Thr Thr Ala Asp Lys Thr Gly Ser Gly Aap Tyr Gly Ser Thr
                240                 245                 250

AAC GAC GCC GGA ATC GCT TTC GGA CCC GAC GGA CAA CGG TTG CTG           1172
Asn Asp Ala Gly Ile Ala Phe Gly Pro Asp Gly Gln Acg Leu Leu
                255                 260                 265

TTG GTG ATG ASG ACG CGA TCG CAG GCC CAS GAC CCC AAG GCC GAG           1217
Leu Val Met Met Thr Arg Ser Gln Ala His Asp Pro Lys Ala Glu
                270                 275                 280

AAC CTG CGA CCG CTC ATC GGT GAG CTG ACG GCG CTG GTG CTG CCG           1262
Asn Leu Arg Pro Leu Ile Gly Glu Leu Thr Ala Leu Val Leu Pro
                285                 290                 295

TCC TTA CTC TGA GTGCTCGACG GATTCGATTG CCGTCGAACC GTTTTCGGTG           1314
Ser Leu Leu
CTCTGGATCG CGATCTGGCG GCTCCGGGCG GGGTTCTGTG TCAACGGCAC ACGTACGGTC     1374
AGGATGCCGC GGTCGTAGCC GGCGGTGAT GTTGTCCTCG TCCGCCTCG                  1424
```

FIG.4C

SA: VHPSTSRSPSRRT

MF:  MTGLSRRNVLIGSLVAAAAVGAGVGGAAPAFAAPIDDQLAELERRDNVLI
SA: ILTATAGAALAAATLVPGTAHASSGGRGHGSGSVSDAERRLAGLERASGARL
AU:          MKKLIFLIVIALVLSACNSNSSHAKE.LNDLEKKYNAHI
                                              α1        β1

MF: GLYAANLQSGRRITHRPDEMFAMCSTFKGYVGCGVLQMAEH.GEISLDNRVF
SA: GVYAYDTGSGRTVAYRADELFPMCSVFKTLSSAAVLRDLDRNGEF.LSRRIL
AU: GVYALDTKSGKEVKFNSDKRFAYASTSKAINSAILLEQVPYNK...LNKKVH
         β2              α2

MF: VDADALVPN....SPVTETRAGA...EMTLAELCQAALQRSDNTAANLLLKT
SA: YTQDD.VEQADGAGPETGKPQNLANAQLTVEELCEVSITASDNCAANLMLRE
AU: INKDDIVAY....SPILEKYVGK...DITLKALIEASMTYSDNTANNKIIKE
           α3            α4           α5

MF: IGGPAAVTAFARSVGDERTRLDRWEVELNSAIPGDPRDTSTPAGLAVGYRAI
SA: LGGPAAVTRFVRSLGDRVTRLDRWEPELNSAEPGRVTDTTSPRAITRTYGRL
AU: IGGIKKVKQRLKELGDKVTNPVRYEIELNYYSPKSKKDTSTPAAFGKTLNKI
       α6              α7                α8

MF: LAGDALSPPQRA...CWKTGCGPIEPRACVPGPEGWTTADKTGSG.DYGSTN
SA: VLGDALNPRDRALLTSWLLANTTSGDRFRAGLPDDWTLGDKTGAG.RYG.TN
AU: IANGKLSKENKKFLLDLMLNNKSGDTLIKDGVPKDYKVADKSGQAITYASEN
         α9           α10        β3      β4

MF: DAGIAFGPDGQRLLLVMMTRSQAHDPKAENLRPLIGELTALVLPSLL
SA: DAGVTWP.PGRAPIVLTVLTAKTEQDAARDDGLVADAARVLAETLG
AU: DVAFVYPKGQSEPIVLLVIFTNKDNKSDKPNDK.LISETAKSVMKEE
           β5                      α11

FIG.5

```
CTCTGTCGTG TATGCGGATG TCAGCCGGAA CGTTCGACAA AGTGGTGCGG GTGACCACCG        60

AAGTTTTGGA AGGTGTTGCC AGAAGACGGG TCACCGCCGA CGAATGCCGG ATCCGCAAAG       120

GCTCGTTGCG CGGTGGGCTG GTGCTCGGCC TGGAGGATTC CGGATCACGT AAGCACCGGA       160

TCGGCCGTAG CGAGCTCAAT TACGGTGAGC ACCGGACCAT CGACCACACG CTGCTGGCCC       240

AGATCGAGGC AGTCACTCTA GAAGAGGTCA ACGCCGTCGC TCACCAGTTC GTGTCGCGGG       300

ACTACGGTGC CGCCGTACTC GGTCCCTATA GTTCGAAAAA GCGCTGCCAC AACAGCTTCA       360

AACTATCGCC GGCTGACCCG CTACACTGGG TCCA    ATG ACC GGA CTA TCG CGA       412
                                         Met Thr Gly Leu Ser Arg

CGC AAC GTT CTG ATC GGT TCG CTC GTG GCG GCA GCT GCC GTC GGT             457
Arg Asn Val Leu Ile Gly Ser Leu Val Ala Ala Ala Ala Val Gly

GCC GGC GTC GGT GGC GCC GCA CCG GCA TTC GCG GCA CCG ATC GAT             502
Ala Gly Val Gly Gly Ala Ala Pro Ala Phe Ala Ala Pro Ile Asp

GAC CAG CTG GCG GAA CTG GAG CGT CGG GAC AAC GTC CTG ATC GGC             547
Asp Gln Leu Ala Glu Leu Glu Arg Arg Asp Asn Val Leu Ile Gly
    α1                                β1
```

FIG.6A

```
                        PstI
TTG TAC GCA GCC AAT CTG CAG TCT GGG CGG AGG ATC ACG CAC CGT          592
Leu Tyr Ala Ala Asn Leu Gln Ser Gly Arg Arg Ile Thr His Arg
                              β2

CCC GAC GAG ATG TTC GCG ATG TGC TCG ACG TTC AAG GGC TAC GTC          632
Pro Asp Glu Met Phe Ala Met Cys Ser Thr Phe Lys Gly Tyr Val
                                        α2

BglII
GGC TGC GGG GTG CTG CAG ATG GCC GAG CAC GGC GAG ATC TCA CTG          677
Gly Cys Gly Val Leu Gln Met Ala Glu His Gly Glu Ile Ser Leu

GAC AAC CGG GTC TTC GTC GAT GCG GAT GCG CTC GTG CCG AAC TCA          722
Asp Asn Arg Val Phe Val Asp Ala Asp Ala Leu Val Pro Asn Ser
                                                         α3

CCC GTC ACC GAG ACA CGT GCC GGT GCC GAG ATG ACG TTG GCC GAG          767
Pro Val Thr Glu Thr Arg Ala Gly Ala Glu Met Thr Leu Ala Glu
                                                     α4

CTG TGC CAG GCG GCG CTG CAG CGC AGT GAC AAC ACC GCG GCG AAC          812
```

FIG.6B

```
Leu Cys Gln Ala Ala Leu│Gln Arg Ser Asp Asn Thr Ala Ala│Asn
                                                         ──
                                                         α5

TTG CTG CTG AAG ACC ATT GGC GGG CCT GCG GCT GTC ACC GCC TTC         857
Leu Leu Leu Lys Thr Ile│Gly Gly│Pro Ala Ala Val Thr Ala Phe
                               α6

GCC CGC AGC GTC GGC GAT GAG CGC ACC CGC CTG GAC CGC TGG GAG         902
Ala Arg Ser Val│Gly Asp Glu Arg Thr Arg Leu Asp Arg Trp│Glu
                                                        ──
                                                        α7

GTA GAG CTG AAC TCC GCG ATA CCC GGG GAC CCG AGG GAC ACC AGC         947
Val Glu Leu Asn Ser Ala│Ile Pro Gly Asp Pro Arg Asp Thr Ser

ACG CCG GCG GGC CTG GCG GTC GGA TAC CGC GCG ATT CTG GCC GGT         992
Thr│Pro Ala Gly Leu Ala Val Gly Tyr Arg Ala Ile│Leu Ala Gly
    α8

GAC GCA CTG AGC CCG CCG CAG CGC GCC TGT TGG AAG ACT GGA TGC         1037
Asp Ala Leu Ser Pro Pro│Gln Arg Ala Cys Trp Lys Thr│Gly Cys
                       α9
```

FIG.6C

```
                              SphI
GGG CCA ATC GAG CCT CGA GCA TGC GTG CCG GGC TTC CCG GAG GGC         1082
Gly Pro Ile |Glu Pro Arg Ala Cys Val Pro Gly| Phe Pro Glu Gly
            α10

TGG ACC ACC GCG GAC AAA ACC GGC AGC GGC GAT TAC GGC AGC ACC         1127
Trp |Thr Thr Ala Asp Lys Thr Gly Ser Gly| Asp Tyr Gly |Ser Thr
     β3                                                 β4

AAC GAC GCC GGA ATC GCT TTC GGA CCC GAC GGA CAA CGG TTG CTG         1172
 Asn Asp Ala Gly Ile Ala Phe Gly| Pro Asp Gly Gln Arg |Leu Leu
                                                        β5

TTG GTG ATG ATG ACG CGA TCG CAG GCC CAT GAC CCC AAG GCC GAG         1217
 Leu Val Met Met Thr Arg Ser Gln Ala| His Asp Pro Lys Ala Glu

AAC CTG CGA CCG CTC ATC GGT GAG CTG ACG GCG CTG GTG CTG CCG         1262
Asn Leu Arg Pro |Leu Ile Gly Glu Leu Thr Ala Leu Val Leu Pro
                 α11

TCC TTA CTC TGA GTGCTCGACG GATTCGATTG CCGTCGAACC GTTTTCGGTG          1314
 Ser Leu Leu|

CTCTGGATCG CGATCTGGCG GCTCCGGCG GGGTTCTGTG TCAACGGCAC ACGTACGGTC     1374

AGGATGCCGC GGTCGTAGCC GGCGGTGAT GTTGTCCTCG TCCGCCTCG                 1424
```

FIG.6D

RECOMBINANT BETA-LACTAMASE, USABLE AS CARRIER MOLECULE IN IMMUNOGENIC COMPOSITIONS

This application is a 371 of PCT/FR93/00151 Feb. 12, 1993.

The object of the present application is novel agents for the preparation of immunogenic compositions and preferably protective vaccinating compositions available in the form of "live vaccines", particles or molecules which can be administered to man or animals.

One of the objectives of the present invention is to suggest agents for the development of immunogenic compositions capable of triggering in man or animals a cellular and/or humoral immune response (through the intermediary of antibodies) against antigenic determinants and in particular against epitopes characteristic of different pathogenic agents. More generally, the invention suggests novel agents to trigger or promote an immune response against any specific epitope to produce antibodies or a cellular immune response, and in particular when the antigenic determinants are of the hapten type and consequently incapable of triggering this immune response by themselves. The invention is also of interest for the purpose of promoting an immune response capable of being conferred by an antigen, and in particular of enhancing the level or nature of the protection.

In this connection the invention describes novel molecules capable of being used as vectors of the antigenicity of different epitopes both in immunogenic compositions containing the hybrid (recombinant) molecules thus formed or in live vaccines.

Different factors can determine the selection of a molecule, in particular of a protein capable of behaving as carrier protein (also called vector) for the purpose of conferring or improving the antigenicity of an epitope heterologous with respect to this molecule. For example, the size parameters of the vector as such and its size with respect to that of the epitope which it will contain as well as the size of the epitope as such must be taken into account. Other constraints for the development of vaccines, live or not, implicating carrier molecules are, for example, the antigenicity of the carrier molecule, its toxicity for a cell host in which it would be produced or for the subject to whom it would be administered. It is also advisable to determine the potential sites of insertion for the epitope and—a matter of some importance when this modified protein is used in the context of the preparation of a live vaccine—its capacity to be exported, even secreted by the host which produces it in order to be accessible to the immune system of the subject to whom the vaccine is administered.

In the context of the present invention the inventors were interested in proteins of the beta-lactamase family, certain properties of which have been studied up to now in a context different from that of the present invention.

The beta-lactamases are enzymes arranged in different classes as a function of their enzymatic activity on different substrates. They are produced by different organisms and in particular by bacteria for example bacteria of the *E. coli, Staphylococcus aureus* type, or also by mycobacteria. These enzymes have been studied for their capacity to protect bacteria against the lethal effects of antibiotics of the beta-lactam type, and hence their capacity to confer on certain bacteria resistance to different antibiotics. It is in this context of the study of the resistance of bacteria to antibiotics that several authors have published articles describing the purification of certain beta-lactamases.

For example, Choubey et al. have published results describing the purification to homogeneity of a beta-lactamase from *Mycobacterium smegmatis* (Microbiology, 1986, vol. 13: 171–175). Other authors have published data relating to the characterization of the beta-lactamase produced in a strain of *Mycobacterium fortuitum*(J. Amicosante et al., Biochem. J., 1990, 271: 729–734; L. Fattorili et al., Antimicrobial Agents and Chemotherapy, September 1991, p. 1760–1764). In this second publication, the authors point out that the beta-lactamases have been described as being periplasmic enzymes in Gram-negative bacteria. In Gram-positives, these enzymes are exported to the surface or released into the medium since there is a single cell membrane. Certain are found in large quantities in the culture medium, others are anchored to the bacterial membrane. These enzymes exhibit a broad spectrum of activity.

The release of this enzyme by the bacteria which produce it would thus be linked in part to environmental factors or to factors intrinsic to the physiology of the cell producing it or also to structural determinants of the beta-lactamase.

In spite of the known characteristics of the beta-lactamases which implicate them in resistance to certain antibiotics and despite the fact that the mode of expression and in particular the possibility of this protein being secreted by the cell which produces it have not been completely characterized, the inventors were interested in the capacity of this enzyme to behave as a vector of the antigenicity of an epitope which would be heterologous to it.

By heterologous epitope is meant here an amino acid sequence characteristic of a protein and in particular of an antigen different from a beta-lactamase, at least different from the beta-lactamase selected as carrier molecule.

According to the inventors they known properties of different beta-lactamases, such as the fact that they are exported and are monomeric as well as their structural properties are capable of conferring many advantages on them for use as vector proteins of the antigenicity of different epitopes. In addition they have been shown to be useful in the context of the development of live vaccines. With a view to defining the conditions to be met for the construction of recombinant proteins from beta-lactamases, the inventors determined the sequence and the structural organization of the gene and predicted the three dimensional structure of the beta-lactamase protein of a mycobacterium *Mycobacterium fortuitum* (designated subsequently as *M. fortuitum*) by modelling. Knowledge of the structure of this gene has made it possible to localize regions suitable for the introduction of a heterologous nucleotide sequence coding for a peptide or a polypeptide carrier of at least one epitope against which it is desired to obtain an immune response and to envisage the preparation of recombinant proteins. IN addition, these researches have made it possible to define which are the sequences which code for a beta-lactamase and the signals necessary for the expression of the products of fusion with the beta-lactamase in which the beta-lactamase is in a stable form and also the signals necessary for the exportation, even secretion of the recombinant protein produced in the cell host.

In addition, the determination of the sequence of the beta-lactamase gene of *M. fortuitum* makes it possible to anticipate the use of other beta-lactamases of similar structure, in particular their three dimensional structure, in order to produce recombinant proteins in the framework of the invention.

In the context of the particular use of these recombinant proteins for the development of live vaccines, the inventors were interested in mycobacteria. An interesting candidate for the development of such vaccines is the mycobacterium *M. bovis* BCG as BCG, used hitherto as a vaccine to protect against tuberculosis. BCG is an avirulent bacterium which exhibits a tropism for the macrophages and is cable of inducing both very strong B and T cell and CTL (cytotoxic T lymphocytes) responses. Its cell wall functions as a very effective adjuvant and a single inoculation can trigger long-term immunity.

The present invention has made it possible to demonstrate that the use of a vector protein such as the beta-lactamase can promote the cloning and expression in mycobacteria, in particular in the BCG, of heterologous antigenic determinants. Advantageously, in the case of the use of BCG as cell host for the expression of the beta-lactamase, recourse will be had to a beta-lactamase which is exogenous compared with those which naturally preexist in the BCG in order to avoid or minimize recombination phenomena.

The invention thus related to a nucleotide sequence characterized in that it is selected from one of the following nucleotide sequences:

the sequence of the gene coding for a beta-lactamase comprising the sequence shown in FIG. 4, (SEQ ID NO:2), any part of the nucleotide sequence show in FIG. 4 (SEQ ID NO:2) contributing to the structure of the beta-lactamase or which is necessary for its expression in a suitable cell hot, in particular the sequence comprised between the nucleotides 1 and 394 of the sequence show in FIG. 4 (SEQ ID NO:2) containing the signals for the expression of the gene, the coding sequence contained in the sequence shown in FIG. 4 (SEQ ID NO:2) and comprising the nucleotides 395 to 1274, any sequence hybridizing under stringent conditions with the sequence shown in FIG. 4 (SEQ ID NO:2) and in particular with the sequence included between the nucleotides 1 to 394 or with the sequence included between the nucleotides 395 and 1274 of this sequence.

Advantageously, sequences corresponding to the preceding specifications are constituted by the nucleotide sequences cloned in the plasmids contained in the *E. coli* strains deposited with the C.N.C.M. under the numbers I-1170 and I1171 as well as any nucleotide sequence which hybridizes with these cloned sequences under stringent conditions.

The sequence shown in FIG. 4 (SEQ ID NO:2) contains the gene coding for the beta-lactamase of *M. fortuitum* as well as the non-coding parts. The nucleotide sequence of the gene for the beta-lactamase of *M. fortuitum* is not the only useful sequence in the framework of the invention; in fact, fragments or a part of the sequence shown in FIG. 4 (SEQ ID NO:2) may be of value.

In particular, an advantageous nucleotide sequence in the context of the invention is the nucleotide sequence corresponding to the non-coding 5' end of the gene for the beta-lactamase, this sequence containing the signals for the expression of the gene for this enzyme. This 5' part of the sequence of the gene may be used for they expression of various nucleotide sequences in cell hosts of they mycobacterium type. It is suitable for example for the expression in mycobacteria of beta-lactamases derived from different organisms of mycobacteria since it contains signals for expression recognized by the mycobacteria.

Other fragments of the nucleotide sequence shown in FIG. 4 (SEQ ID NO:2) which can be used in the framework of the invention are the sequences coding for a truncated protein whose overall structure is preserved compared with the native protein, in particular under conditions such that the expression product of this nucleotide sequence is stable and in particular insensitive to the cellular proteases of the host which produces it and/or possibly the subject to whom it is administered.

By stability of the protein is meant in particular the possibility to purify it or the possibility for this protein to be recognized by an antibody.

An advantageous nucleotide sequence is a sequence exhibiting similarities with the sequence shown in FIG. 4 (SEQ ID NO:2). By similarity is meant in particular the capacity to hybridize with the sequence shown in FIG. 4 (SEQ ID NO:2) under stringent conditions.

In order to determine whether the nucleotide sequence is capable of hybridizing under stringent conditions with the coding sequence contained in the sequence shown in FIG. 4 (SEQ ID NO:2), the following test is used:

For example, a specific probe is used starting from the coding sequence shown in FIG. 5 (SEQ ID NO:4–6) with which it is desired to test the hybridization of a specific sequence, this probe is labelled with 32 p ($10^6$ cpm/ml) and it is placed in contact with the test sequence for 16 hours at 65° C. in a hybridization solution (50% formamide, 5×SSPE, salmon sperm DNA 200 µg/ml and 10×Denhardt). The membranes on which the hybridization is performed are then washed twice for 30 minutes with a 1×SSC, 0.1% SDS solution at room temperature (20° C.), then washed twice with 0.1×SSC, 0.1% SDS for 30 minutes at 65° C.

| Composition of 5 × SSPE: | |
|---|---|
| NaCl | 900 mM |
| NaH$_2$PO$_4$ | 450 mM |
| Na$_2$EDTA | 5 mM |
| pH | 7.4 |
| Denhardt: | |
| Ficoll | 2.5 g/l |
| Polyvinylpyrrolidone | 2.5 g/l |
| BSA (Pentex fraction V) | 2.5 g/l |
| 0.1 × SSC: | |
| NaCl | 15 mM |
| Na$_3$ citrate | 0.1% |

According to another definition, a nucleotide sequence of the invention is characterized in that it codes for a protein of the beta-lactamase type consisting of the amino acid sequence shown in FIG. 4 (SEQ ID NO:2).

The invention moreover relates to a recombinant nucleotide sequence characterized in that it comprises:

a nucleotide sequence corresponding to one of the preceding specifications coding for a beta-lactamase modified by at least one heterologous nucleotide sequence coding for a heterologous peptide sequence comprising at least one epitope, the modification being made at at least one site which makes possible the exposure of the epitope at the surface of the beta-lactamase or it accessibility to the solvent when the recombinant sequence is expressed, a nucleotide sequence corresponding to the preceding specifications coding for a truncated beta-lactamase, modified by at least one heterologous nucleotide sequence coding for a heterologous peptide sequence comprising at least one epitope, the modification being made at at least one site which makes possible the exposure of the epitope at the surface of the beta-lactamase or it accessibility to the solvent when the recombinant sequence is expressed, and the hybrid protein expressed conserving the essential structural characteristics of the native beta-lactamase, in particular those which confer on it its recognition by antibodies directed against the epitope(s) or its stability when it is recombined.

The exposure of the heterologous epitope i the recombinant protein is reflected in the accessibility of this epitope to the solvent, in particular to water molecules or in the availability of this epitope for presentation to antibodies.

According to the specification given in the preceding paragraph, the nucleotide sequence coding for the beta-lactamase or for a truncated beta-lactamase may be modified by at least one heterologous nucleotide sequence. In fact just as the size of the heterologous nucleotide sequence does not constitute a priori a limiting parameter, the insertion of several heterologous sequences can be envisaged within the sequence coding for the beta-lactamase or for a truncated beta-lactamase.

The insertion of heterologous sequences comprising at least one epitope and possessing a size of several nucleotides would seem to be advantageous to the extent that the problems which may result from a deformation of the modified beta-lactamase coded by the recombinant nucleotide sequence of the invention are limited. However, it is possible to insert at one or more sites of the nucleotide sequences coding for the beta-lactamase longer heterologous nucleotide sequences provided that they code for a peptide sequence, the epitope or epitopes of which are exposed at the surface of the recombinant protein formed or which are accessible to the solvent. Preferably the hybrid thus formed conserves the most important characteristics of its structure, in particular its capacity to be recognized by anti-beta-lactamase antibodies and anti-heterologous sequence antibodies, as well as its capacity to be purified.

A so-called stable protein according to the invention exhibits at least one of the following properties:

the enzymatic activity of the beta-lactamase, optionally modified in magnitude the capacity to be recognized by an antibody, in particular an anti-beta-lactamase antibody, or an antibody directed against a heterologous epitope which it contains in the case of a recombinant protein or, an insensitivity to degradation by cellular proteases, the possibility to be purified.

Different heterologous nucleotide sequences may be selected in order to produce the recombinant nucleotide sequences of the invention. A first group of heterologous sequences is characterized in that it comprises sequences coding for a peptide or a polypeptide implicated in the virulence of a pathogenic agent or, generally, for an antigen with protective potential against a factor produced as a consequence of an infection. In this respect a characteristic sequence of a pathogenic organism is for example a sequence of a virus, parasite, bacterium or fungus (for example of the Aspergillus genus). In particular mention should be made in the framework of the present invention of sequences of bacteria such as *M. leprae, M. tuberculosis, M. intracellulare, M. africanum, M. avium,* the bacilli responsible for diphtheria, tetanus, Salmonella, certain treponema, pertussis toxin, sequences of other microorganisms such as the sporozoites and merozoites of plasmodium, the sequences of Leishmania or Schistosoma, Shigella, Neisseria, Borrelia, viral sequences, in particular the viruses responsible for mumps, german measles, measles, herpes, influenza, the viruses responsible for rabies, polio, hepatitis and AIDS HIV, HTLV-I, HTLV-II and SIV as well as oncogenic viruses.

The nucleic acid sequence to be expressed may also code for an immunogenic sequence such as that of a snake or insect venom.

As an example, a useful heterologous nucleotide sequence is for example a sequence coding for a peptide sequence of an antigen of a human retrovirus of type HIV, in particular an envelope, *gag, nef* or *pol* antigen of a HIV-1 or HIV-2 retrovirus.

Other useful sequences are the immunogenic sequences of mycobacteria, in particular the proteins or the fragments of the proteins corresponding to genes implicated in virulence and antigens with protective potential. An antigen is said to have "protective potential" when it is capable of triggering or promoting a protective immune response, in particular by production of antibodies or by induction of a cell-mediated immune response, in particular of the CTL type. Such an antigen with protective potential may be constituted by an epitope, even a hapten insufficient i itself to trigger the immune response.

The invention thus allows the preparation of useful recombinant proteins, in particular for the constitution of immunogenic compositions in which the epitope exposed at the surface of the recombinant protein is characteristic of a hormone, for example, or any substance whose biological effects it is desired to attenuate, even neutralize.

Advantageously, a recombinant nucleotide sequence may be constituted by a nucleotide sequence coding for a beta-lactamase or a truncated beta-lactamase such as that described previously in which would be inserted a heterologous sequence coding for the peptide sequence V3 of the envelope antigen of the different HIV-1 variants or a longer sequence of the envelope of a HIV virus. This sequence has been described in the publication by K. Javaherian et al. (Proc. Natl. Acad. Sci. USA 86: 6768–6772, 1989). Advantageously, the heterologous sequence coding for the peptide sequence V3 is inserted at the *BGl*II site of the sequence coding for the beta-lactamase.

The invention also relates to a replicative or integrative recombinant cloning and/or expression vector characterized in that it is modified at one of its sites inessential for its replication or its integration by a recombinant nucleotide sequence described above.

Interestingly, the recombinant nucleotide sequence contained in the vector is under the control of the expression promoter of the beta-lactamase corresponding to the sequence.

When this vector is modified only by a sequence coding entirely or partially for the beta-lactamase, it may also comprise expression signals for translation and even secretion of different origin from that of the beta-lactamase selected as a function of the host in which it is desired to clone or express this recombinant vector.

As an example of vectors for the preparation of recombinant vectors according to the invention, mention may be made of plasmids, phages or transposons.

In particular, a plasmid of the invention is the plasmid pACYC184BlaM containing the *Sph* I fragment of the sequence of the beta-lactamase of *M. fortuitum* shown in FIG. 4 and which was deposited with the C.N.C.M. (Collection Nationale des Microorganismes, Paris, France) in an *E. coli* strain HB101 (pACYC184BlaM) under the number I-1171 deposited on 11 Feb. 1992.

The plasmid pACYC184BlaM contains the *Sph* I/*Sph* I fragment of about 4.7 kb of the genomic DNA of *M. fortuitum* D316 which hybridizes with the probe Bla01. This fragment bears the first 834 bases of the gene coding for a class A beta-lactamase as well as its regulatory regions.

The culture medium recommended for this strain is an L-broth medium plus chloramphenicol (30 $\mu$g/ml) and inoculation is carried out in an L-broth medium, the incubation temperature being about 37° C. with shaking.

Another preferred plasmid according to the invention contains the gene for the beta-lactamase of *M. fortuitum*; it is the plasmid pIPJ39 contained in a strain of *E. coli* MC1061, (pIPJ39) deposited with the C.N.C.M. on 11 Feb. 1992 under the number I-1170.

The plasmid pIPJ39 contains the BamHI/BamHIII fragment of about 6 kb of the genomic DNA of *M. fortuitum* FC1 which hybridizes with the probe Bla01. This fragment bears the gene coding for a class A beta-lactamase as well as flanking regions.

The culture medium recommended for this strain is an L-broth medium plus ampicillin (100 µg/ml) and inoculation is carried out in an L-broth medium and the incubation temperature is about 37° C. with shaking.

The object of the invention is also a recombinant cell host characterized in that is transformed by a recombinant nucleotide sequence described above or by a recombinant vector described above under conditions which allow the expression of the recombinant nucleotide sequence in the form of a stable fusion protein and its exposure or its exportation at the surface of the host or its secretion into the extracellular medium.

Many cell hosts may be modified by a recombinant nucleotide sequence or a recombinant vector according to the invention.

A suitable procedure for the preparation of recombinant cell hosts according to the invention is for example electroporation in conformity with the description of Snapper S et al. (1988, PNAS USA 85: 6985–6991) or conjugation according to the procedure of Lazraq R et al. for example (1990, FEMS Microbiol. Lett. 69: 135–138), or according to the procedure of Gormley E. P. and Davies J. (J. Bacteriol., 173: 6705–6708).

Advantageously, recourse will be had to mycobacteria when the sequence coding for the beta-lactamase is a sequence originating in a mycobacterium. In fact in this case the transfer of the gene coding for a beta-lactamase of a mycobacterium into a strain of mycobacteria facilitates the expression of this sequence in as much as the recognition and expression signals, even signals for secretion, contained in the beta-lactamase gene are recognized by the host mycobacteria. Generally, it will be possible to have recourse to an Actinomycetes strain and in particular an avirulent strain or strain rendered avirulent, by making sure that the recognition signals are suitable for the expression of the recombinant sequence or the recombinant vector introduced into the strain.

In a manner particularly preferred for the realization of the invention recourse will be had to the BCG strain. The invention thus relates to a strain of BCG transformed by a recombinant nucleotide sequence or a recombinant vector of the invention which enables a recombinant protein (hybrid protein) to be exposed at the surface of the cell under conditions which ensure the exposure of the epitope or epitopes against which it is desired to induce an immune response.

A hybrid protein is said to be exposed when it is extracellular but remains anchored to a point of the surface of the cell which produces it. In a particularly useful manner the nucleotide sequences of the invention will be expressed such that the expression products are secreted at the exterior of the cell which produces them and consequently released into the medium.

Other cell hosts according to the invention are bacteria, a non- virulent *E. coli* strain or a non-virulent strain of enterobateria such as an avirulent Salmonella strain provided that the above recombinant nucleotide sequence or the recombinant vector which transforms the bacterium is place under the control expression signals recognized by this bacterium.

Other interesting micro-organisms are for example fungi such as the Aspergillus.

In the case of the use as cell hosts of prokaryotic or eukaryotic cells not belonging to the group of the mycobacteria, recourse will be had to the use of expression signals which can be recognized by the cell hosts in order to obtain the expression, even the secretion, of the recombinant protein containing the beta-lactamase or a truncated beta-lactamase as well as the heterologous peptide sequence.

Other systems for the expression of the recombinant beta-lactamase according to the invention may be constituted for example by animal cells, for example insect cells or mammalian cells such as CHO cells. In this case the vectors suitable for the insertion of the DNA or the cDNA or even the RNA into these cells may be viruses or plasmids. Other systems such as yeast systems such *Saccharomyces cerevisiae* may also be appropriate.

By exposed site is meant a site which allows access to or the recognition of the heterologous peptide sequence and in particular access to or recognition of the epitope or epitopes with a view to obtaining an immune response. An exposed site is either a site present on the surface of the beta-lactamase protein or a site contained in this protein whose epitope is still recognized by the antibodies for example even when the protein is denatured.

As an example the possibility may be mention according to which the heterologous peptide sequence is inserted upstream from a site normally unexposed at the surface of the beta-lactamase protein, this site being exposed as a result of the insertion of the heterologous sequence, for example as a consequence of folding resulting from interactions between the beta-lactamase protein and the heterologous sequences. In selecting the insertion site in the beta-lactamase protein, it will be advantageous to select sites which allow the overall structure of the protein, and consequently its stability, to be conserved.

The knowledge acquired by the inventors concerning the sequence of the beta-lactamase gene of *M. fortuitum* has allowed them to localize the different regions of the alpha helix and beta pleated sheet type responsible for the three-dimensional conformation of this protein. Consequently the inventors have been able to determine with the aid of the three-dimensional structure of the beta-lactamase of *S. aureus* and *S. albus* G which might be the domains appropriate for the insertion of heterologous peptide sequences which avoid the impairment of the structure of the native protein under conditions which would be prejudicial to its value as a carrier molecule. Thus the authors have established the possibility of inserting the heterologous peptide sequences preferably in a domain of a beta-lactamase outside the regions structured in alpha helices and beta sheets.

A heterologous peptide sequence is preferably inserted in the beta-lactamase of *M. fortuitum* in the region forming the junction between the alpha helix 2 and the alpha helix 3 of the beta-lactamase.

Other preferred insertion sites are constituted by the regions comprised between the beta pleated sheet 2 and the alpha helix 2, between the alpha helix 3 and the alpha helix 4 or also between the beta pleated sheet 4 and the beta pleated sheet 5.

According to an advantageous embodiment of the invention, the heterologous sequence may also be inserted in the C-terminal part of the beta-lactamase sequence.

For the preparation of recombinant proteins involving beta-lactamases of different origin, it will be advantageous to determine the localization of the alpha helices and beta pleated sheets which confer their structure relative to the data obtained for the beta-lactamase of S. aureus.

The insertion is preferably carried out such that the heterologous peptide sequence is accessible to the water molecules of the environment.

Figure 9:
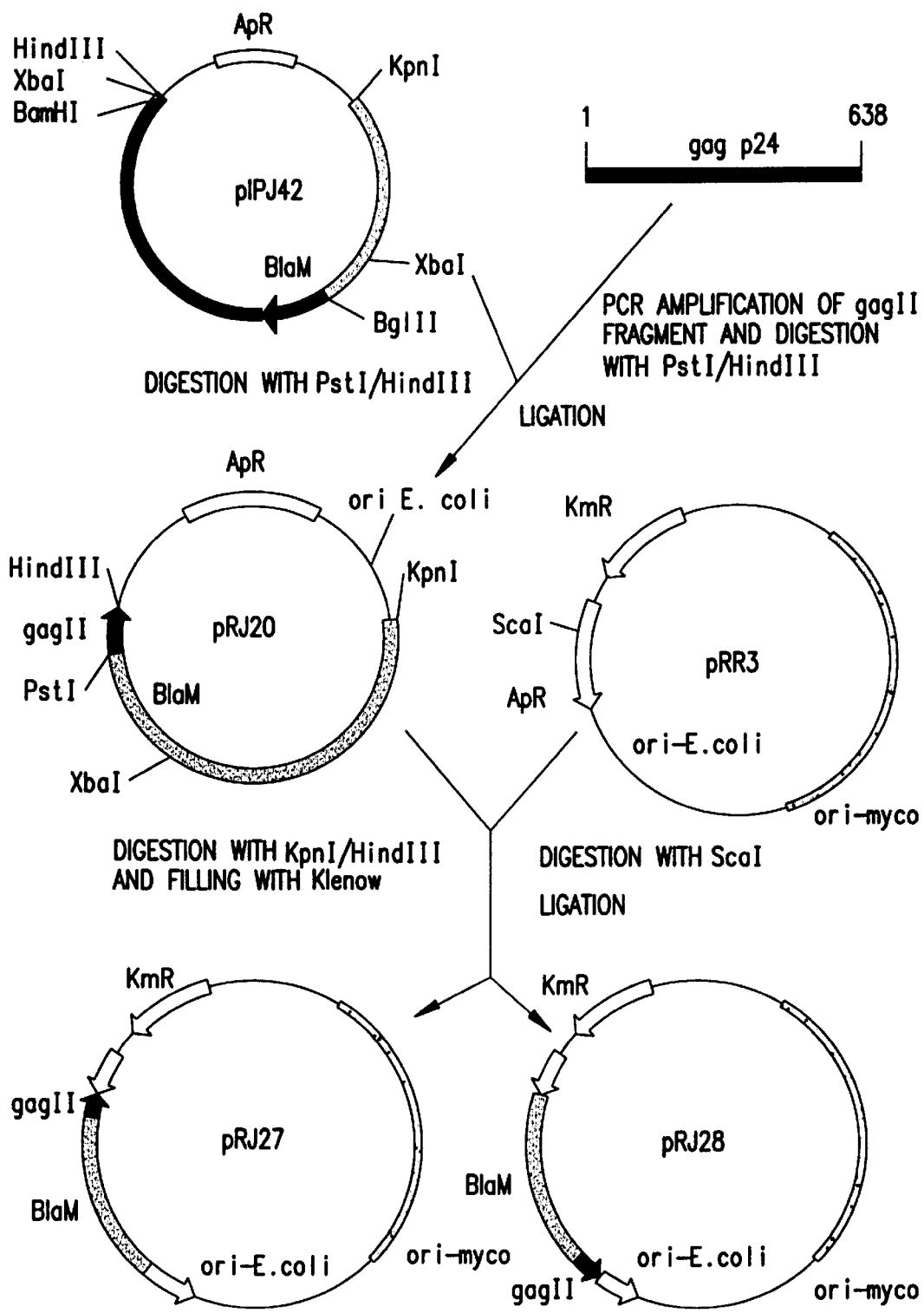

The heterologous sequences likely to be inserted in the beta-lactamase or in a truncated beta-lactamase are the sequences which were described above in the part which relates to the nucleotide sequences. For example, they are sequences of the HIV retrovirus, in particular sequences of the envelope glycoprotein, the gag, nef or pol proteins of a HIV-1 or HIV-2 retrovirus. As an example mention will be made of the peptide V3 of the envelope HIV-1.

The invention allows the construction of recombinant beta-lactamase proteins in which the insertion of the heterologous sequence bearing the epitope is accompanied by a deletion of a part of the beta-lactamase. According to an advantageous embodiment the invention also allows the heterologous sequence to be inserted without deletion from the beta-lactamase.

For example, this insertion may be achieved at the C-terminus of the beta-lactamase without deletion of any part of the sequence of the latter.

The object of the invention is also an immunogenic composition characterized in that it comprises a recombinant BCG strain described above in combination with a suitable pharmaceutical vehicle for its administration to man or animals.

Such a composition is capable of constituting a live vaccine. It may be administered by injection or by an other suitable route. Such an immunogenic composition may be used to trigger the immune response, for example to trigger the cellular response and optionally to trigger the production of protective antibodies or also to contribute to the production of these antibodies in a host to which it is administered. The invention relates not only to the production of vaccinating compositions which can be administered to man but also to the preparation of compositions for vaccination purposes in veterinary medicine.

The immunogenic composition of the invention may also be used as a booster composition to stimulate the production of antibodies initiated by the administration of a protein or another constituent of the pathogenic agent or more generally the agent against which an immune response is sought.

The invention preferably relates to an immunogenic composition characterized in that the recombinant strain which it contains is a *M. bovis* strain of the BCG type corresponding to the specifications given previously. A particular BCG strain is the avirulent strain of the INSTITUTE PASTEUR No. 1137P2, used for the commercial vaccine against tuberculosis.

As pharmaceutical vehicle suitable for the production of the immunogenic compositions of the invention, mention may be made of the physiologically acceptable excipients usually used, in particular neutral or acidic excipients and for example magnesium stearate, polyvinylpyrrolidone or alcohols. This immunogenic composition may also include adjuvants of the immune response composition may also include adjuvants of the immune response such as Freund's complete or incomplete adjuvant, aluminium hydroxide, muramyl dipeptide derivatives, a metabolizing oil such as squalene.

In the case in which a live vaccine is used, the usual doses for vaccination with BCG should be used.

Another immunogenic composition of the invention is characterized in that it comprises a recombinant protein complying with the above specifications in combination with a pharmaceutical vehicle suitable for its administration. This composition, like the immunogenic composition composing the live vaccine, may be used to trigger the immune response or in the form of a booster composition.

Other advantages and characteristics of the invention will become apparent in the Examples which follow and in the Figures which are described below.

LEGENDS TO FIGURES

FIG. 1

Nucleotide sequence of the probe BlaM1 (SEQ ID NO:1)

FIG. 2

Plasmid pACYC184 recombined with an insert of about 4,7 kb of the beta-lactamase gene.

FIG. 3

Plasmid pIPJ39 recombined with the beta-lactamase gene.

FIG. 4

Sequence of the genetic region bearing the gene coding for the beta-lactamase of *M. fortuitum.*

The nucleotide sequence is indicated in capital letters and is numbered in the right hand column. The peptide sequence (SEQ ID NOS:2–3) of the beta-lactamase is indicated with the three letter code under the nucleotide sequence to which it corresponds. The numbering is indicated below the sequence.

The nucleotide sequence of nt1 to nt1061 was determined from plasmid pIPJ319.

FIG. 5

MF: *Mycobacterium fortuitum* (SEQ ID NO:4 )

SA; *Streptomyces albus* (SEQ ID NO:5)

NU: *Staphylococcus aureus* (SEQ ID NO:6 )

The position of the insertions to be made is indicated by dotted lines.

The position of the alpha helices and the beta plated sheets is indicated below the sequence of *S. aureus.*

The predictions of the structure of *M. fortuitum* are indicated above its sequence.

FIG. 6

Position of the structural motifs predicted for the beta-lactamases of *M. fortuitum* (SEQ ID NOS:7–8)

The different alpha helices and beta pleated sheets are indicated by rectangles. The nucleotide sequence and the position of several restriction sites are also indicated on this figure.

FIG. 7—Construction of the Plasmid pIPJ46

The plasmid pAL817 is a derivative of pAL5000 and is described in the publication by Ranes et al., J. Bacteriol. 172: 2793–2797 (1990). The cassette containing the kanamycin resistance gene of the transposon Tn903 and the plasmid pSL1180 are obtained from the Pharmacia company.

FIG. 8—Construction of the Plasmids pIPJ64 and pIPJ65

The amplification of the V3 fragment is performed starting from the plasmid pTG5167 supplied by Transgene. The plasmid pIPJ42 is a derivative of pIPJ39 in which the *Bgl*II/*Bam*HI fragment, corresponding to the promoter and to the amino-terminal fragment of the gene coding for the beta-lactamase of *Mycobacterium fortuitum* FC1 has been replaced by the *Bgl*II/*Bgl*II fragment of pACYC184 corresponding to the promoter and to the amino-terminal fragment of the gene coding for the beta-lactamase of *Mycobacterium fortuitum* D316. The plasmid pTG5167 is a derivative of pTG186poly (Guy et al., 1987) in which a *Bgl*II/*Eco*RI fragment bearing the gene coding for the protein GP160 of HIV1/MN was cloned in the polylinker.

FIG. 9—Construction of the Plasmids pRJ27 and pRJ28

The amplification of the gagII fragment is performed starting from the plasmid pTG2103 supplied by Transgene. The plasmid pTG2103 is a derivative of pTG959 (Guy et al., 1987) in which a a *Bgl*II/*Eco*RI fragment bearing the gene coding for the protein P24 of HIV1/LAI was cloned in the polylinker.

Figure 10:
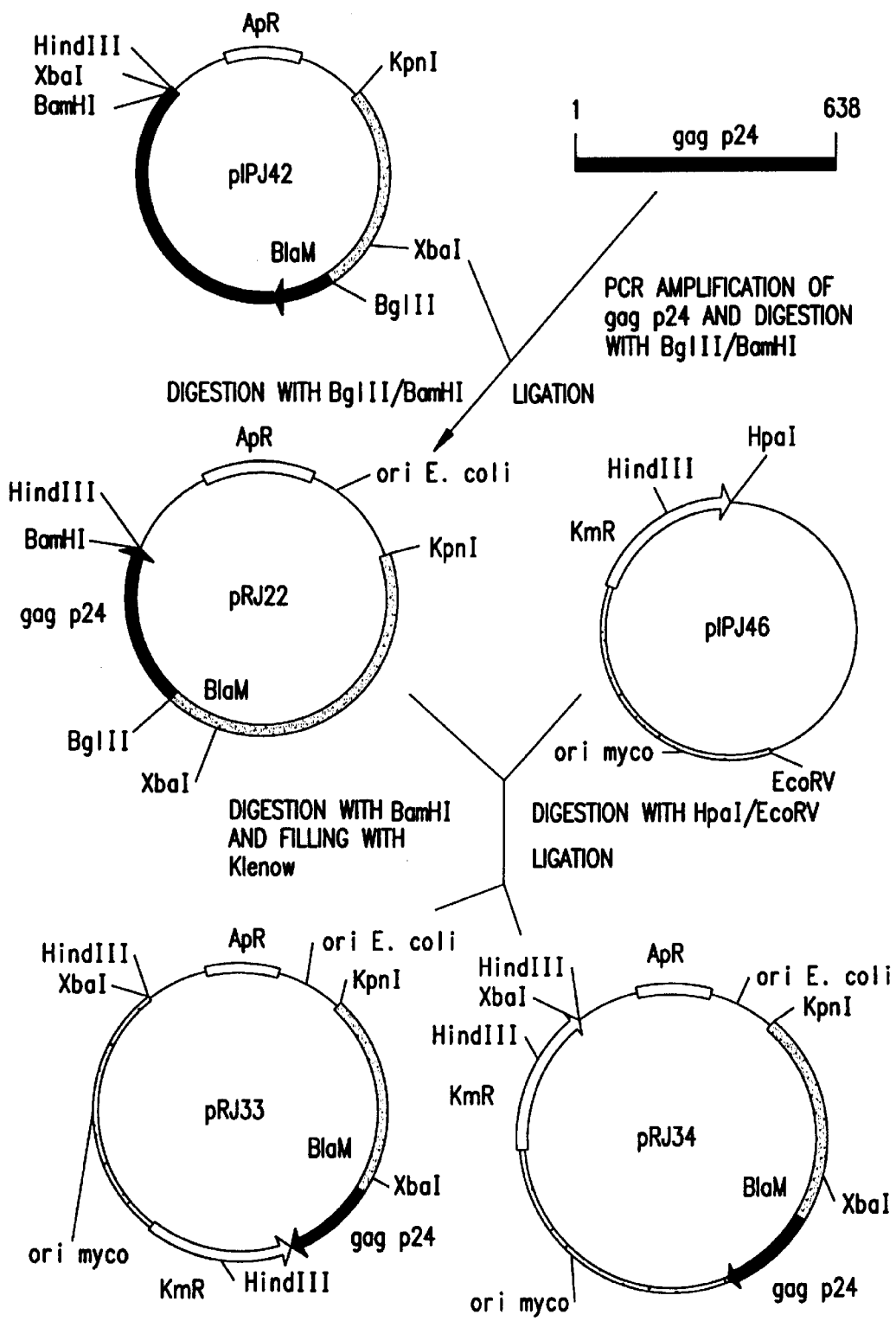

FIG. 10—Construction of the Plasmids pRJ33 pRJ34

The amplification of the fragment Gap p24 is performed starting from the plasmid pTG2103 supplied by Transgene.

Figure 11:
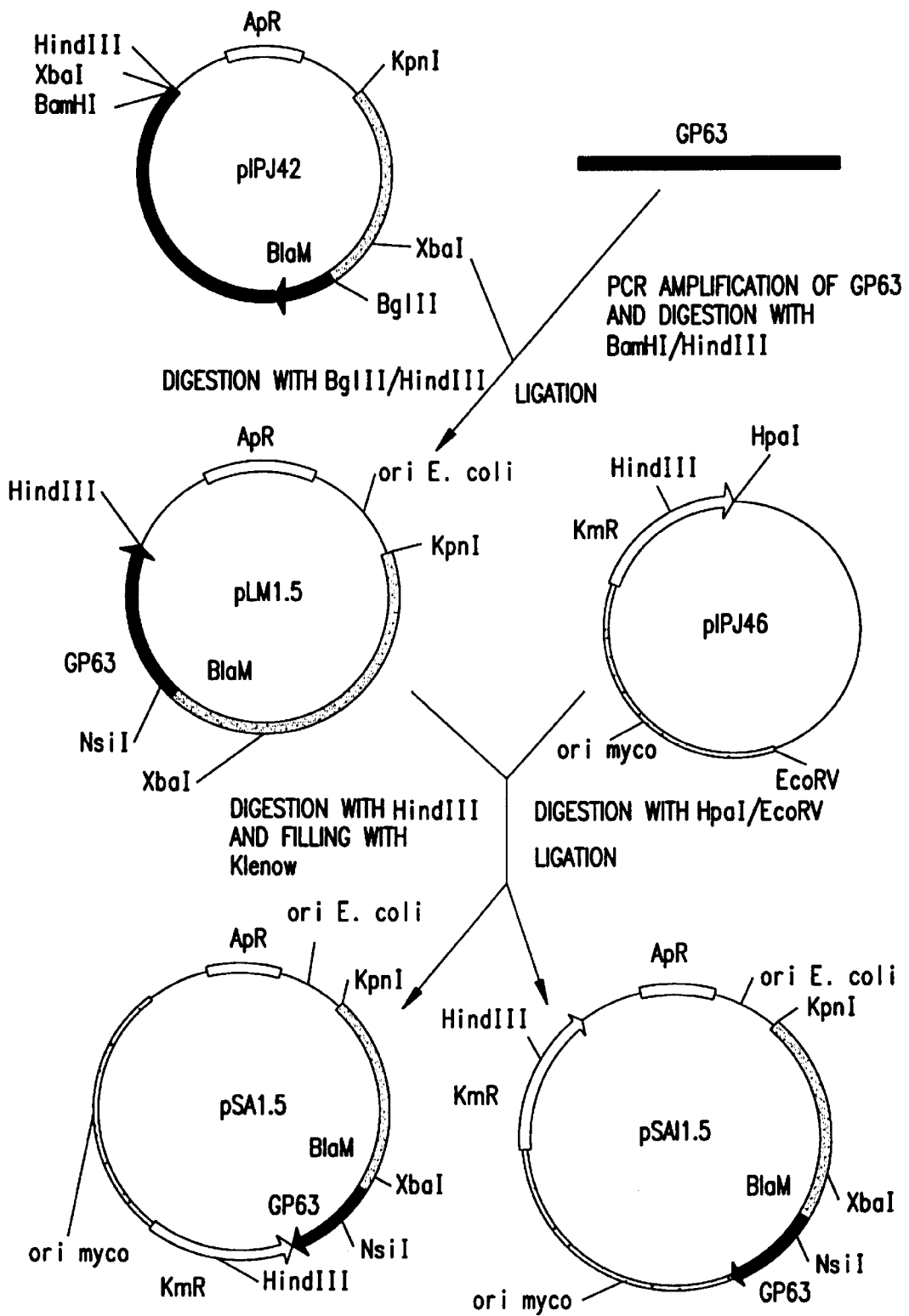

FIG. 11—Construction of the Plasmids pSA1.5 pSAI1.5

The amplification of the gene coding for the protein GP63 of *Leishmania major* is performed directly from the chromosome of this parasite.

Figure 12:
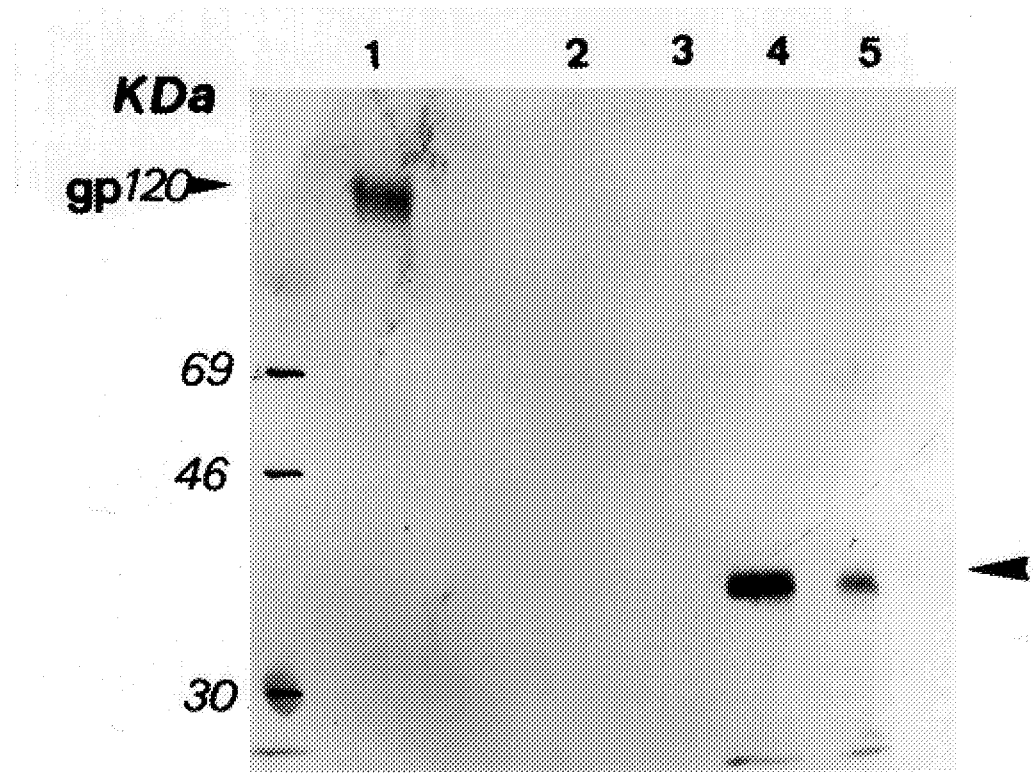

FIG. 12—Western blot analysis of the expression of the beta-lactamase-V3 polypeptide. The molecular weight markers are indicated on the left of line 1.

Line 1: protein gp 120; line 2: supernatant of standard BCG; line 3: extract of standard BCG; line 4: supernatant of recombinant BCG bearing the plasmid pIPJ64; line 5: extract of recombinant BCG bearing the plasmid pIPJ64.

Figure 13:
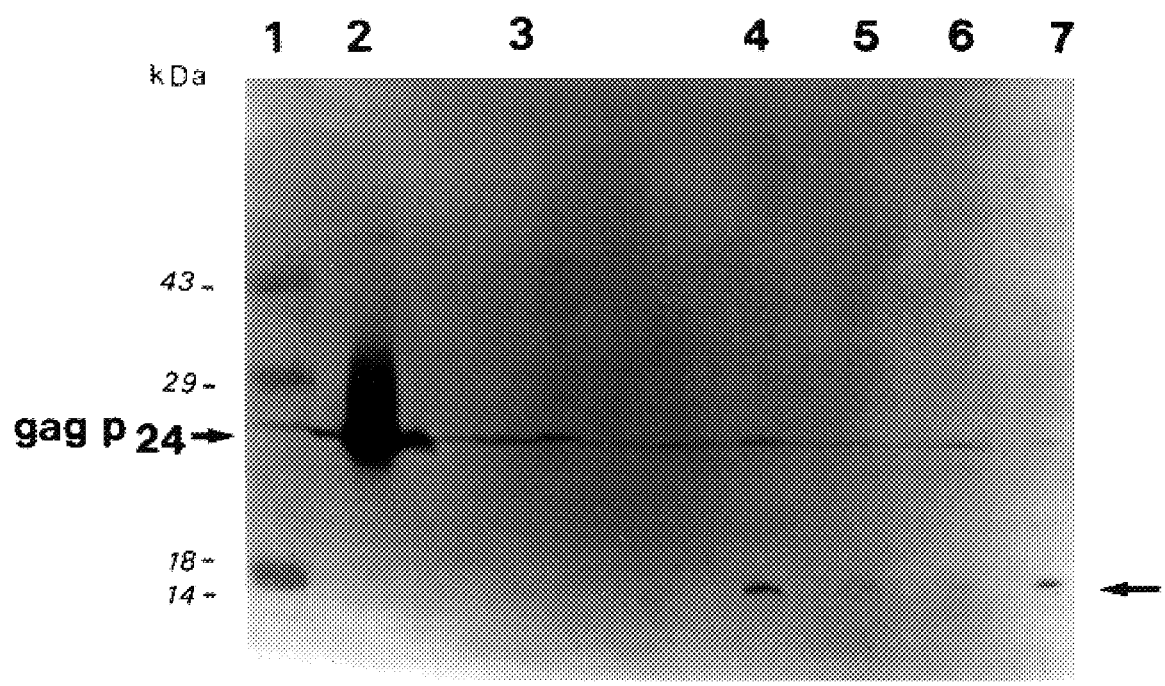

FIG. 13—Western blot analysis of the expression of the beta-lactamase-GagII polypeptide.

Line 1: molecular weight markers; line 2: protein Gag P24; line: extract of standard BCG; lines 4 and 5: extracts of BCG recombinants bearing the plasmid pRJ28; lines 6 and 7: extracts of BCG recombinants bearing the plasmid pRJ27.

Figure 14:
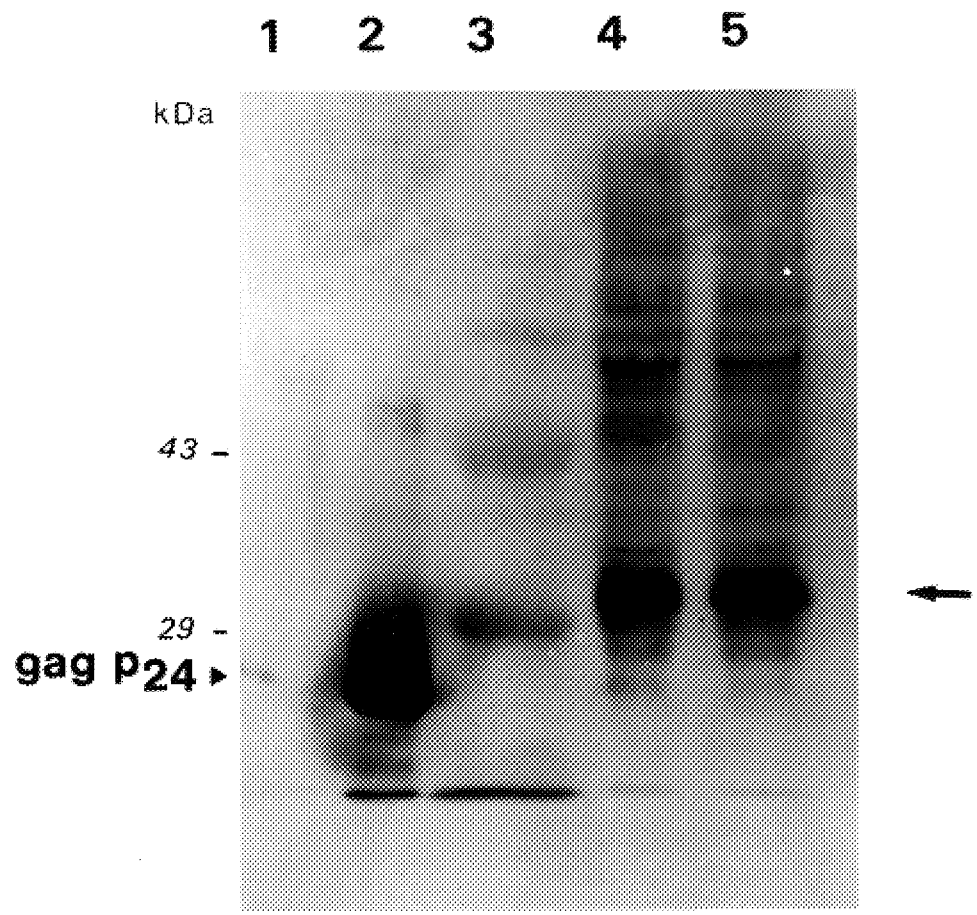

FIG. 14—Western blot analysis of the expression of the beta-lactamase-Gag P24 polypeptide Line 1: extract of standard BCG; line 2: protein Gag P24; line 3: molecular weight markers; lines 4 and 5: extracts of recombinant BCG bearing the plasmids pRJ33 and pRJ34, respectively.

Figure 15:
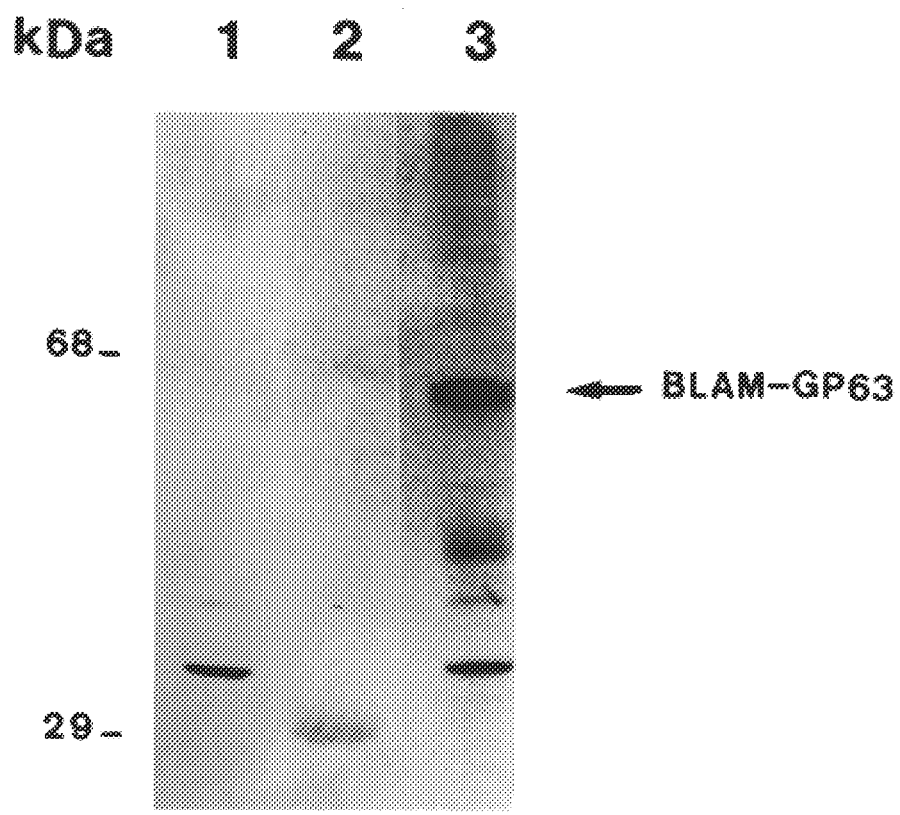

FIG. 15—Western blot analysis of the expression of the beta-lactamase-GP63 polypeptide.

Line 1: extract of standard BCG; line 2: molecular weight markers; line 3: extract of recombinant BCG bearing pSAI1.5

FIG. 16—Proliferative responses of the cells extracted from the lymph glands of the mice inoculated with the BCG bearing the plasmid pRJ28.

4 Balb/c mice are given an intradermal injection of $10^7$ cfu of BCG-pRJ28, 4 others are given standard BCG 1173P2. After 14 days the peripheral lymph glands are removed for the proliferation test.

The protein Gag P24 of HIV1LAI is used to induce the proliferation of the lymph node cells which had been in contact with the fusion protein BlaM-V3 produced by the recombinant BCG.

EXPERIMENTAL PART

In the example which follows a mycobacterial beta-lactamase was used with a view to its expression in *M. bovis* BCG, the expression signals being adapted to the mycobacterial context.

Figure 3:
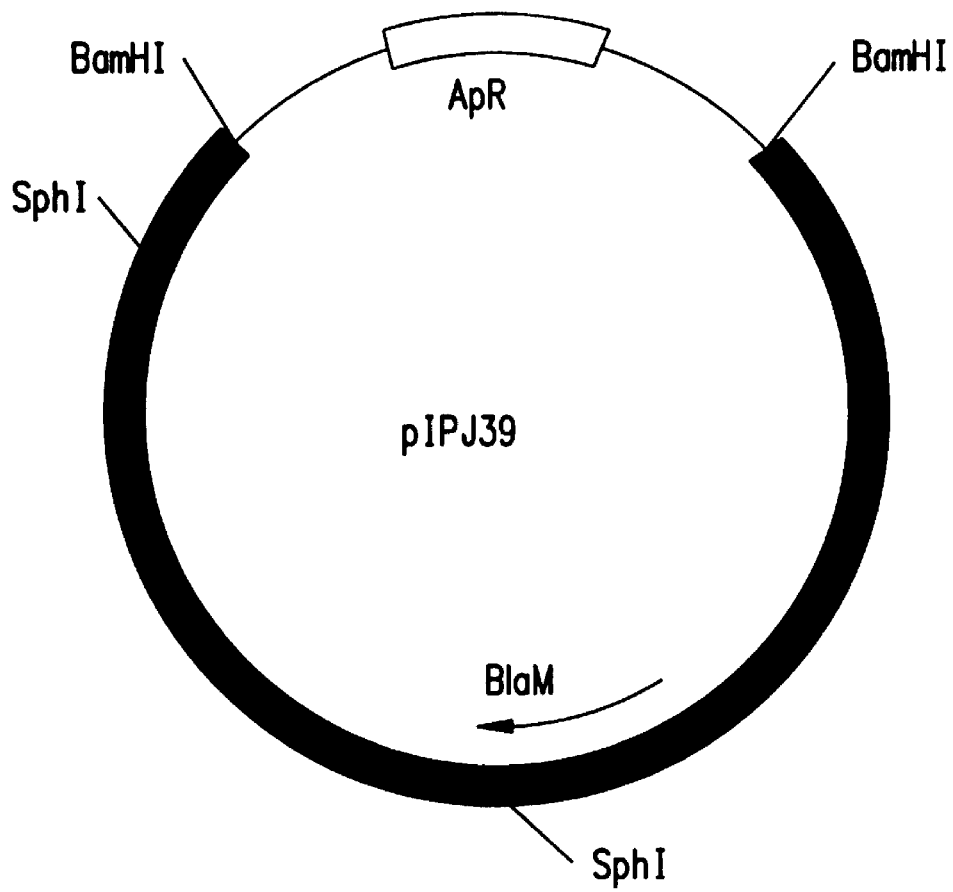
Figure 7:
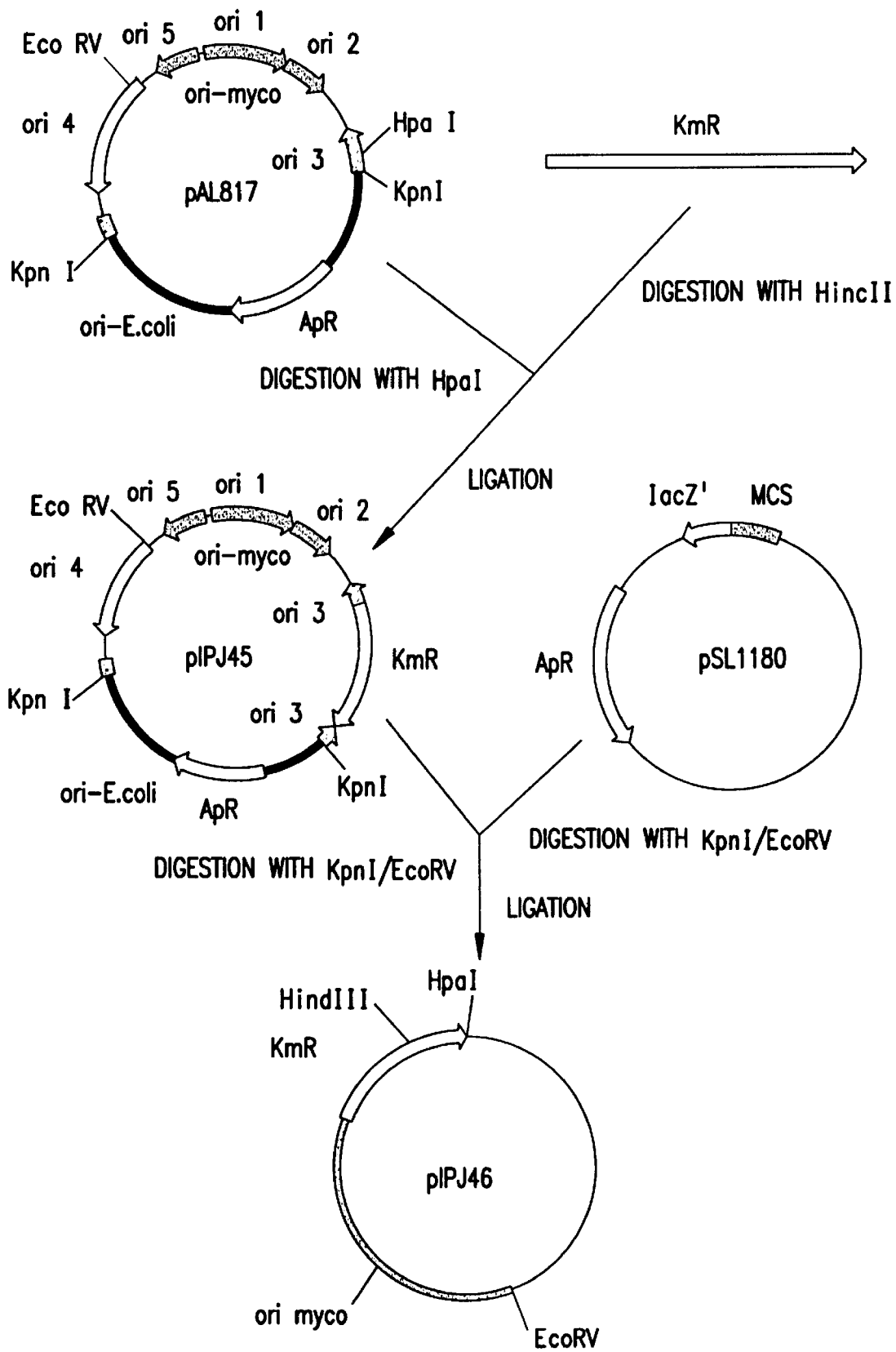
Figure 8:
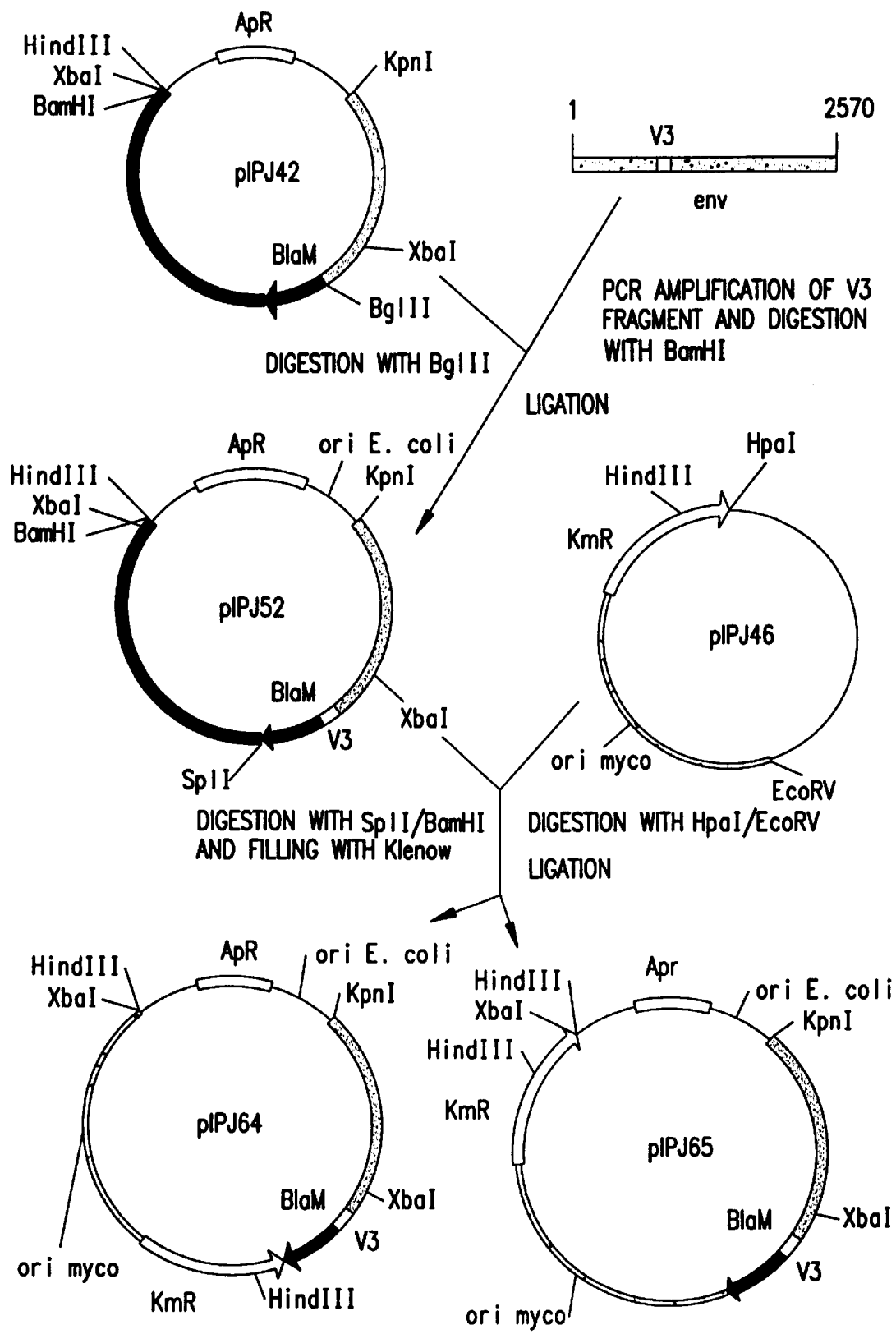

A beta-lactamase of *M. fortuitum* has previously been purified by Amicosante et al. and Fattorili et al from a mutant strain which produces this enzyme in considerable quantities. The N-terminal sequence of the beta-lactamase was determined by Amicosante et al. to be:

APIDDQLAELERRDNVLIGLYAANLQS-GRRITHRPDEMFAMXSTFKGYV (SEQ ID NO:9)

X corresponds to a residue not determined.

I order to isolate the gene coding for this protein, a DNA probe, BlaM1, corresponding to the gene fragment coding for this N-terminal part of the protein was synthesized by PCR. In order to do that two mixtures of oligonucleotides were synthesized by making use of the degeneracy of the genetic code, and the preferential use of the codons i the mycobacteria (J. Dale and A. Pakti, Molecular Biology of the Mycobacteria, Surrey University Press, Guilford, UK 1990, p. 173–198); The amino acid sequence APIDDQ (SEQ ID NO:10) is thus probably coded by a family of DNA sequences whose formula is indicated by the following consensus:

5' GC (CorG) CC(GorC) ATC GA(CorT) GA(CorT) CAG 3' (SEQ ID NO:11)

The nucleotides are indicated in capital letters; each oligonucleotide belonging to the family is determined by selecting one of the nucleotides indicated in parentheses. The mixture of these oligonucleotides called Moligo1 was synthesized chemically by incorporating one or other of the nucleotides indicated in parentheses. We used the Cyclone oligonucleotide synthesizer (Biosearch USA).

The second mixture of oligonucleotides, called Moligo2 is constituted of oliognucleotides corresponding to the complementary strands of the DNA sequences coding for the C-terminal part of the N-terminal fragment indicated above, namely STFKGYV (SEQ ID NO:12).

Using the same nomenclature as that above the oligonucleotides constituting the Moligo2 mixture correspond to the consensus:

5' AG(CorG) TG(CorG) AAG TTC CC(GorA) AT(AorG) CA(GorC) 3' (SEQ ID NO:13)

One of the mixtures contains oligonucleotides of sequence identical with or very similar to the 5' part of BlaM1, the second mixture contains oligonucleotides complementary to the 3' part of BlaM1. These two mixtures are used to synthesize the probe BlaM1 by means of PCR from the DNA which we have extracted from *M. fortuitum* FC1 (C. Martin et al., Nature vol. 345: 739–743, 1990). The probe BlaM1 was sequenced (FIG. 1). Starting from this sequence the oligonucleotide Bla01:

5' CTTGAAGGTCGAGCACATCGCGAACAT 3' (SEQ ID NO:14) was synthesized and radioactively labelled in order to use it as probe to detect in a *M. fortuitum* D316 gene bank (Amicosante et al.) a clone processing a fragment bearing the gene coding for the beta-lactamase. This bank was constructed by cutting the chromosomal DNA of *M. fortuitum* D316 with the restriction enzyme *Sph* I and by cloning the fragments randomly in the vector pACYC184. The *Sph* I fragments were inserted at the *Sph* I site of pACYC184 and the HB101 strain of *E. coli* was transformed by this ligation mixture in the presence of calcium chloride. The transformants were selected on LB medium plates containing 30 μg/ml of chloramphenicol. The resistant strains obtained were subcultured on solid LB medium containing 25 μg/ml of tetracycline and only those sensitive to this antibiotic were retained. A transformant clone containing a fragment which hybridizes with Bla01 was isolated. This clone contains a recombinant plasmid pACYC184 with an insert of about 4.7 kb which hybridizes with Bla01. The restriction map of this plasmid was constructed (FIG. 2) and the region hybridizing with Bla01 was sequenced. The nucleotide sequence is shown in FIG. 4. The analysis of this sequence shows a reading frame which possesses similarities with other class A beta-lactamases. We have thus concluded from it that is must be the structural gene for the beta-lactamase of *M. fortuitum*. The sequenced *Sph* I fragment only contains a part of the gene. A *Bgl*II-*Sph*I restriction fragment (shown by thick black curve in FIG. 2) within the gene called Bla02 was used as probe; the entire gene was cloned starting from a *M. fortuitum* FC1 bank. This bank was constructed by cloning *Bam*HI chromosomal fragments from 4 to 10 kb isolated by electrophoresis on agarose gel and cloned at the *Bam*HI site of the plasmid pUC18 which was linearised by cutting at this site and dephosphorylated. The transformant clones were selected on LB medium plates containing 100 μg/ml of ampicillin. A transformant clone which hybridizes with the probe Bla02 was isolated. It contains a recombinant plasmid bearing an insert of about 6 kb which hybridizes with the probe Bla02. The restriction map of this insert was constructed (FIG. 3) and the region which hybridizes with the probe was sequenced. It contains the C-terminus of the gene (FIG. 4). The two gene fragments obtained from the *Sph*I and *Bam*HI banks have a common part which makes it possible to reconstitute the entire gene; it is shown in FIG. 4 with the amino acid sequence of the protein deduced from the nucleotide sequence. The amino acid sequence possesses similarities with the sequences of other known class A beta-lactamases. An alignment of the sequences of the beta-lactamases of *M. fortuitum, S. albus, S aureus* is suggested in FIG. 5. The position of the different structural motifs, alpha helices and beta sheets determined for the beta-lactamase of *S. aureus* is indicated on the primary structure of this enzyme in the same figure. According to the similarities between the primary structure of the beta-lactamase of *M. fortuitum* which we have deduced from the gene whose structure we have determined and that of *S. aureus*, the position of the structural motifs is suggested in FIG. 5. In FIG. 6, the structural motifs of the beta-lactamase of *M. fortuitum* as well as the nucleotide sequence of the gene are also shown. A region forming the junction between the alpha helix 2 and alpha helix 3 ought to correspond to an extended region within which it will be possible to introduce epitopes without modifying the general structure of the protein. The gene fragment coding for this region nt648 to nt719 contains a unique *Bgl*II site which will be used for the insertion of foreign DNA fragments coding for various epitopes. Three other regions seem interesting for the insertion of epitopes: the region nt585 to nt613,making possible an insertion between the beta pleated sheet2 and the alpha helix2, the region nt744 to nt748 making possible an insertion between the alpha helix 3 and alpha helix 4, and nt1152 to nt1167 which should make possible the insertion of epitopes between the beta pleated sheet 4 and beta pleated sheet 5.

The insertion of epitopes at the C-terminal position of the protein, i.e. near to nucleotide 1043, might also be useful.

In order to analyse the expression of the BlaM gene the latter was fused with beta-galactosidase, an enzyme easy to determine and whose expression in bacteria is easily detectable on a Petri dish. In order to do this a *BGl*II-*Pst*I fragment of 1598 pb containing a part of the blaM gene and the region upstream was isolated and inserted between the *Bam*HI and *Pst*I sites of the plasmid pNM482. The resulting fusion blaM-lacZ was then transferred to an *E. coli*-mycobacterium shuttle vector and this construction was used to transform *E. coli* and *M. smegmatis* by electroporation.

The expression of the *lac*Z gene was observed uniquely in *M. smegmatis*. These results show that the cloned region situated upstream from the blaM gene is sufficent to induce the expression of the gene and that it must consequently contain most of the initiation signals of transcription and translation. These signals are specific for the mycobacteria. Hence, as a result, they will advantageously be used for the expression of any gene cloned under their control in the form of fusion operon or fusion protein.

The fact that the blaM-lacZ fusion is functional shows that the blaM system will be used for the expression of various heterologous genes or gene fragments in the mycobacteria. Depending on the gene fusions performed, the resulting fusion proteins will be localized in the cytoplasm, be exported to the exterior of the bacterium into the culture medium or remain anchored to the external membrane.

Examples of the use of the promoter Pbla associated with all or part of the gene coding for the beta-lactamase which it controls expressions of viral or parasite antigens or antigen fragments and induction of specific immune responses by the BCG expressing one of these antigens.

The promoter Pbla (beta-lactamase promoter) associated with the gene coding for the beta-lactamase was used to express several viral antigenic motifs of HIV-1. (The sequences are given in connection with the publication "Human retrovirus and AIDS 1991" a compilation and analysis of nucleic acid and amino acid sequences, edited by Myers G. et al., published by theoretical Biology and Physics, Group T-10, Mail Stop K710, Los Almos National Laboratory, Los Alamos, N. Mex. 877545 USA) or the antigen GP63 of Leishmania. (The sequences are given in connection with the publication: Button, L. L. and McMaster, W. R. (1988) Molecular cloning of the major surface antigen of Leishmania. J. Exp. 167. 724–729) in *M. smegmatis* and/or the BCG.

The antigenic motif V3 of HIV-1 strain MN and an env fragment of this same strain were expressed in *M. smegmatis* and/or the BCG.

The antigen Gag P24 of IV-1 strain LAI as well as a fragment of this latter (GagII) were expressed in BCG. The major surface protein of *Leishmania major* and *Leishmania infantum* GP63 were also expressed by the BCG.

In the case of the expression of the GagII fragment only the results of the immune responses directed against Gag are reported. A specific cellular response was observed.

1) The fragment of the env gene coding for the V3 determinant from amino acid 303 to amino acid 338 (HIV strain MN) was inserted at the *Bgl*II site of the gene coding for the beta-lactamase on the plasmid pIPJ42. In order to do this a fragment coding for this determinant was synthesized by PCR. Two oligonucleotides V3I. (ATTGGATCCTGGTACCCGAGGAGTGTACAAGACCCAACTACAATAA) and V3II (TTTGGATCCCTCTAGACCCGTCGCCACAATGTGCTTGTCTTATAGTTCCT) were synthesized by the GENSET company. They served to amplify the env fragment from the plasmid pTG5167 bearing it and supplied by TRANSGENE. (FIG. 8). The amplified fragment bears the *Bam*HI restriction site at its ends. It is cut by the corresponding restriction enzyme and cloned in the plasmid pIPJ42. The recombinant plasmid bearing the fragment coding for the determinant V3 is called pIPJ52. In this plasmid a cassette containing the origin of replication in the mycobacteria (ori myco of pAL5000) and kanamycin resistance gene of Tn903 was inserted between the *Spl*I and *Bam*HI sites. This cassette is the *Eco*RV/*Hpa*I fragment isolated from the plasmid pIPJ46 (FIG. 8). The plasmids resulting from the insertion of the *Eco*RV/*Hpa*I fragment in pIPJ52 in one or the other orientation are pIPJ64 and pIPJ65.

The plasmids pIPJ64 and pIPJ65 were transferred into *M. smegmatis* and the BCG by electroporation. The fusion polypeptide expressed by the plasmids pIPJ64 and pIPJ65 consists of the insertion of the V3 motif between the alpha helix 2 and the alpha helix 3 of the beta-lactamase. This polypeptide is detected in the culture medium of the strains of *M. smegmatis* and BCG transformed by the plasmids pIPJ64 pIPJ65 by means of Western blot using the monoclonal antibody F5-5 provided by the Hybridolab of the Pasteur Institute.

2) The fragment of the gene coding for the Gag part (HIV-1 strain LAI) from amino acid 233 to amino acid 307 (GagII) was inserted at the *PstI* site of the gene coding for the beta-lactamase on the plasmid pIPJ42. In order to do this, a fragment containing the part of the gag gene coding for GagII was synthesized in vitro by PCR Two oligonucleotides NG1 (AAACTGCAGGGATCCATGGG-AAGTGACATAGCA) and NG2 (CCCTGAAGCTTACT-CGGCTCTTAGAGTTTT) (SEQ ID NO: 18) were synthesized in a CYCLONE DNA synthesizer. They served to amplify the fragment coding for GagII starting from the plasmid pTG2103 bearing it and supplied by TRANSGENE. The amplified fragment bears the PstI and HindIII sites. It is cut by the corresponding enzymes and cloned in the plasmid pIPJ42 between the PstI and HindIII sites. The resulting plasmid is called pRJ20. Starting from this plasmid, the KpnI/HindIII fragment coding for the beta-lactamase-GagII fusion was inserted at the ScaI site of pRR3 (Ranes, M. G., Rauzier, J., Lagranderie, M., Georghiu, M. and Gicquel, B. (1990) Functional analysis of pAL5000, a plasmid from *Mycobacterium fortuitum*: construction of a "mini" Mycobacterium-*Escherichia coli* shuttle vectro. J. Bacteriol. 172, 2793–2797) in the two orientations. The resulting plasmids have been called pRJ27 and pRJ28. The plasmids pRJ27 and pRJ28 were transferred to *M. smegmatis* and the BCG by electroporation.

The fusion polypeptide expressed by the plasmids pRJ27 and pRJ28 consists in the fusion between an amino-terminal fragment of 24 amino acids of the beta-lactamase and the gagII fragment since a stop codon is situated at the end of gagII. The beta-lactamase-GagII fusion polypeptide is not found in the culture medium of *M. smegmatis* or the BCG transformed by pRJ27 and pRJ28 but in the cytoplasm of these bacteria. It is detected by Western blot in bacterial extracts (performed according to Winter, N., Lagranderie, M., Rauzier, J., Timm, J., Lecrec, C., Guy, B., Kieny, M. P., Gheorghiu, M., Gicquel, B. (1991) Expression of heterologous genes in *Mycobacterium bovis* BCG: induction of a cellular response against HIV-1 Nef protein. Gene 190, 47–54) by using the monoclonal antibody 1542 obtained from the Hybridolab of the Pasteur Institute.

After inoculation of Balb/c mice by the BCG expressing the beta-lactamase-GagII fusion, an immune response of the cellular type directed against Gag was observed by using proliferation tests on lymph node cells after stimulation by the protein Gag P24. The protocol used is similar to that described by Winter et al. The details are given in FIG. 13.

It is probable that they are CD4 and CD8 T lymphocytes.

3) The protein Gag P24 of HIV-1 strain LAI

The fragment coding for the protein GagP24 was inserted at the BglII site of the gene coding for the beta-lactamase on the plasmid pIPJ42. In order to do this a fragment coding for Gag P24 was synthesized in vitro by PCR starting from the plasmid pTG2103 supplied by TRANSGENE With the aid of the oligonucleotides JGAG1 (CGAATTCAGATCTCA-ACTTTAAATGCATGGGTA) (SEQ ID NO: 19) and EML5 (GTTCGAATTCTCACAAACTCTTGC) (SEQ ID NO: 20) synthesized beforehand on a CYCLONE synthesizer. The amplified fragment bears the BglII and BamHI sites. It is cut by the corresponding enzymes and cloned in the plasmid pIPJ42 between the BglII and BamHI sites. The resulting plasmid is called pRJ22. As in the case of the construction of the plasmids pIPJ64 and pIPJ65, the cassette containing the origin of replication in the mycobacteria (ori myco of pAL5000) and the kanamycin resistance gene of Tn903 was inserted between the SplI and BamHI sites. It is the EcoRV/HpaI fragment isolated from the plasmid pIPJ46 (FIG. 10). These plasmids resulting from the insertion of the EcoRV/HpaI fragment are called pRJ33 and pRJ34. The plasmids pRJ33 and pRJ34 were transferred into *M. smegmatis* and the BCG by electroporation. The fusion polypeptide expressed by the plasmids pRJ33 and pRJ34 consists of an amino-terminal fragment of 60 amino acids of the beta-lactamase with the protein GagP42 since a stop codon is situated at the end of the gagP24 gene cloned here. In a similar manner to the beta-lactamase-GagII fusion, the fusion polypeptide beta-lactamase-GagP24 is not found in the culture medium but in the cytoplasm. It is detected by means of Western blot using the monoclonal antibody 1113 obtained from the Hybridolab of the Institute Pasteur.

4) The surface antigen GP63 of *Leishmania infantum* and *Leishmania major*

The fragment coding for the protein GP63 lacking the transmembrane C-terminal part was inserted at the BglII site of the gene coding for the beta-lactamase on the plasmid pIPJ42. In order to do this, a fragment coding for the antigen GP63 was synthesized in vitro by PCR. Two oligonucleotides GP631 (GCGGGATCCTTATGCATGTG-CGCGACGTGAACTGGGGC) (SEQ ID NO: 21) and GP632 (CCGAATTCAAGCTTCTACGCCGTGTTGCCG-CCGTCCTT) (SEQ ID NO: 22) served to amplify this fragment starting from the chromosomal DNA of the *Leishmania infantum* and *Leishmania major* strains.

The ends of the amplified fragments possess BamHI and HindIII sites. They are cut by the corresponding enzymes and inserted between the BglII and HindIII sites of pIPJ42. The resulting plasmid is called pLM1.5.

As in the case of the construction of the plasmids pIPJ64 and pIPJ65, the cassette containing the origin of replication in the mycobacteria (ori myco of pAL5000) and the kanamycin resistance gene of Tn903 was inserted between the SplI and BamHI sites.

It is the EcoRV/HpaI fragment isolated from the plasmid pIPJ46 (FIG. 11).

The plasmids resulting from the insertion of the EcoRV/HpaI fragment in one or other of the two orientations are called pSA1.5 and pSAI1.5.

The plasmids pSA1.5 and pSAI1.5 were transferred into *M. smegmatis* and the BCG by electroporation. The fusion polypeptides expressed by these plasmids consist of the fusion between an amino-terminal fragment of 60 amino acids of the beta-lactamase with the protein GP63 from which the transmembrane C-terminal part is deleted. As in the case of the fusions with Gag, the fusion polypeptides beta-lactamase-protein GP63 are found in the cytoplasm of *M. smegmatis* and the BCG transformed by the plasmids pSA1.5 and pSAI1.5. They are detected by a monoclonal antibody directed against the protein GP63 purified from extracts of a recombinant *E. coli* strains expressing this protein. This monoclonal antibody has been described by Handman, L. Button, and R. W. McMaster/(1990) *Leishmania major*; Production of recombinant gp63, its antigenicity and immunogenicity in mice Exp. Parasitol. 70, 427–435/ (FIG. 15).

We claim:

1. An isolated polynucleotide, comprising a sequence selected from the group consisting of:
   a sequence of the gene coding for a beta-lactamase, comprising the sequence shown in FIG. 4 (SEQ ID NO: 2),
   a sequence having the sequence between nucleotides 1 and 394 of the sequence shown in FIG. 4 (SEQ ID NO: 2) containing the signals for the expression of the gene,
   the coding sequence contained in the sequence shown in FIG. 4 (SEQ ID NO: 2) and comprising the nucleotides 395 to 1274, and
   any sequence hybridizing under stringent conditions with the sequence shown in FIG. 4 (SEQ ID NO: 2), the sequence included between the nucleotides 1 and 394 or with the sequence included between the nucleotides 395 and 1274 of the sequence of FIG. 4 (SEQ ID NO: 2).

2. An isolated polynucleotide which codes for a beta-lactamase protein comprising the amino acid sequence shown in FIG. 4 (SEQ ID NO: 2).

3. A recombinant polynucleotide having a sequence selected from the group consisting of:
   a nucleotide sequence according to claim 2 coding for a beta-lactamase, into which is inserted at least one heterologous nucleotide sequence coding for a heterologous peptide sequence comprising at least one epitope, the insertion being made at at least one site permitting the exposure of the epitope at the surface of the beta-lactamase or its accessibility to the solvent when the recombinant sequence is expressed, and
   a nucleotide sequence according to claim 2 coding for a truncated beta-lactamase, into which is inserted at least one heterologous nucleotide sequence coding for a heterologous peptide sequence comprising at least one epitope, the insertion being made at at least one site permitting the exposure of the epitope at the surface of the beta-lactamase or its accessibility to the solvent when the recombinant sequence is expressed, and the essential structural characteristics of the native beta-lactamase are conserved in the hybrid protein expressed from said sequence, wherein said essential structural characteristics confer stability, and recognition by antibodies.

4. The recombinant polynucleotide according to claim 3, wherein the heterologous nucleotide sequence contained codes for a peptide sequence implicated in the virulence of a pathogenic agent, or for an antigen with protective potential.

5. The recombinant polynucleotide according to claim 3, wherein the heterologous nucleotide sequence contained codes for a peptide sequence of an antigen of a human HIV type retrovirus.

6. The recombinant polynucleotide of claim 5, wherein said antigen of a human HIV type retrovirus is selected from the group consisting of envelope, gag, nef, and pol antigens of HIV-1 and HIV-2 retroviruses.

7. The recombinant polynucleotide according to claim 3, wherein the heterologous nucleotide sequence contained codes for the peptide sequence V3 of the envelope antigen of HIV-1.

8. The recombinant polynucleotide according to claim 3, wherein the heterologous nucleotide sequence is inserted in a region located between the alpha helices and the beta pleated sheets of the sequence of the beta-lactamase shown in FIG. 6 (SEQ ID NO: 8).

9. The recombinant polynucleotide according to claim 8, wherein the insertion site is contained in a region of the sequence shown in FIG. 6 (SEQ ID NO: 7) selected from:
   the region between the beta pleated sheet 2 and the alpha helix 2 corresponding to the nucleotides 585 to 613,
   the region between the alpha helix 2 and alpha helix 3, corresponding to the nucleotides 648 to 719,
   the region between the alpha helix 3 and alpha helix 4, corresponding to the nucleotides 744 to 748, and
   the region between the beta pleated sheets 4 and 5 corresponding to the nucleotides 1152 to 1167.

10. A recombinant vector for cloning, expression or both, which contains a nucleotide sequence according to claim 1 inserted at a site non-essential for replication of integration of the vector.

11. The recombinant vector according to claim 10, wherein the inserted nucleotide sequence is placed under the control of the promoter of the beta-lactamase gene from which the nucleotide sequence is derived.

12. The recombinant vector according to claim 10, wherein the vector is a plasmid, phage or a transposon.

13. The recombinant vector according to claim 10, wherein the vector is the plasmid pIPJ39 containing the beta-lactamase gene of M. fortuitum, this plasmid being contained in an E. coli strain deposited with the C.N.C.M. on the 11 Feb. 1992 under the number I-1170.

14. The recombinant vector according to claim 10, wherein the vector is the plasmid pACYC184 containing the Sph I fragment of the sequence shown in FIG. 4 (SEQ ID NO: 2), contained in an E. coli strain deposited with the C.N.C.M. on 11 Feb. 1992 under the number I-1171.

15. A recombinant cell host, which is transformed by a nucleotide sequence according to claim 1 or by a recombinant vector according to claim 10 such that said host cell permits the expression of the recombinant nucleotide sequence in the form of a stable fusion protein or its exportation to the surface of the host or its secretion into the medium.

16. The recombinant cell host according to claim 15, wherein the cell host is a strain of Actinolycetes, avirulent or made avirulent.

17. The recombinant cell host according to claim 16, wherein said strain of Actinomycetes is a strain of mycobacteria.

18. The recombinant cell host according to claim 15, wherein the cell host is M. bovis BCG.

19. The recombinant cell host according to claim 15, wherein the cell host is a bacterium selected from the group consisting of non-virulent E. Coli strains and non-virulent strains of enterobacteria, provided that the recombinant nucleotide sequence or the recombinant vector contained is placed under the control of expression signals recognized by the bacterium.

20. The recombinant cell host according to claim 19, wherein said non-virulent strains of enterobacteria are avirulent Salmonella.

21. The recombinant cell host according to claim 15, wherein the cell host is a fungus, provided that the recombinant nucleotide sequence or the recombinant vector contained is placed under the control of expression signals recognized by the fungus.

22. The recombinant cell host according to claim 21, wherein said fungus is a fungus of the Aspergillus genus.

23. An immunogenic composition, comprising a recombinant avirulent cell host according to claim 15 and a pharmaceutical vehicle suitable for its administration.

24. The immunogenic composition according to claim 23, wherein said avirulent cell host is a recombinant strain of *M. bovis* BCG.

25. A recombinant protein, which is a beta-lactamase coded by a nucleotide sequence according to claim 1 into which is inserted at an exposed site at least one heterologous peptide sequence bearing at least one antigenic epitope under conditions such that the recombinant protein induces an immune response against the heterologous polypeptide(s) in animals or man.

26. The recombinant protein according to claim 25, wherein the structure of the beta-lactamase is essentially conserved such that the recombinant protein is stable and is insensitive to cellular proteases.

27. The recombinant protein according to claim 25, wherein the beta-lactamase is a class A beta-lactamase.

28. The recombinant protein according to claim 25, wherein the beta-lactamase is that of *M. fortuitum.*

29. The recombinant protein according to claim 25, wherein the beta-lactamase is in the active form.

30. The recombinant protein according to claim 25, wherein the heterologous peptide sequence which it contains is accessible to the solvent.

31. The recombinant protein according to claim 25, wherein the recombinant protein contains at least one heterologous peptide sequence bearing at least one epitope inserted at a side present in a region of the beta-lactamase outside of the regions structured in alpha helices or beta pleated sheets.

32. The recombinant protein according to claim 25, wherein the recombinant protein contains at least one heterologous peptide sequence bearing at least one epitope inserted in a region forming a junction between the alpha helix 2 and the alpha helix 3 of the beta-lactamase.

33. The recombinant protein according to claim 25, wherein the recombinant protein contains at least one heterologous peptide sequence bearing at least one epitope inserted in a region forming a juncture between the alpha helix 3 and the alpha helix 4 of the beta-lactamase.

34. The recombinant protein according to claim 25, wherein the recombinant protein contains at least one heterologous peptide sequence bearing at least one epitope inserted in a region forming a juncture between the beta pleated sheet 4 and the beta pleated sheet 5 of the beta-lactamase.

35. The recombinant protein according to claim 25, wherein the recombinant protein contains at least one heterologous peptide sequence bearing at least one epitope inserted in an exposed region of the C-terminal sequence of the beta-lactamase.

36. The recombinant protein according to claim 25, wherein the recombinant protein contains as heterologous peptide sequence a peptide sequence of the HIV retrovirus.

37. The recombinant protein according to claim 36, wherein said peptide sequence of the HIV retrovirus is a member selected from the group consisting of the envelope glycoprotein and gag, nef, and pol proteins of the HIV-1 and HIV-2 retroviruses.

38. The recombinant protein according to claim 25, wherein the recombinant protein contains as heterologous peptide sequence the V3 peptide of the envelope of HIV-1.

39. The recombinant protein according to claim 38, which is encoded by a nucleotide sequence consisting of the nucleotide sequence coding for the V3 peptide of the envelope of HIV-1 inserted at a Bgl II site of a polynucleotide sequence selected from the group consisting of:

a sequence of the gene coding for a beta-lactamase, comprising the sequence shown in FIG. 4 (SEQ ID NO: 2), and the coding sequence contained in the sequence shown in FIG. 4 (SEQ ID NO: 2) and comprising the nucleotides 395 to 1274.

40. A recombinant polynucleotide comprising a portion of the nucleotide sequence located between nucleotides 1 to 394 of the sequence shown in FIG. 4 (SEQ ID NO: 2) containing the expression signals for the gene and a heterologous nucleotide sequence under the control of said expression signals.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 145 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GCCCCGATCG ATGATCAGCT GGCGGAACTG GAGCGTCGGG ACAACGTCCT GATCGGCTTG      60

TACGCAGCCA ATCTGCAGTC TGGGCGGAGG ATCACGCACC GTCTCGACGA GATGTTCGCG     120

ATGTGCTCGA CGTTCAAGGG TTATG                                          145
```

( 2 ) INFORMATION FOR SEQ ID NO:2:

( i ) SEQUENCE CHARACTERISTICS:
        ( A ) LENGTH: 1426 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 395..1276

( x i ) SEQUENCE DESCRIPTION: SEQ ID NO:2:

```
CTCTGTCGTG TATGCGGATG TCAGCCGGAA CGTTCGACAA AGTGGTGCGG GTGACCACCG      60

AAGTTTTGGA AGGTGTTGCC AGAAGACGGG TCACCGCCGA CGAATGCCGG ATCCGCAAAG     120

GCTCGTTGCG CGGTGGGCTG GTGCTCGGCC TGGAGGATTC CGGATACGT AAGCACCGGA     180

TCGGCCGTAG CGAGCTCAAT TACGGTGAGC ACCGGACCAT CGACCACACG CTGCTGGCCC     240

AGATCGAGGC AGTCACTCTA GAAGAGGTCA ACGCCGTCGC TCACCAGTTC GTGTCGCGGG     300

ACTACGGTGC CGCCGTACTC GGTCCCTATA GTTCGAAAAA GCGCTGCCAC AACAGCTTCA     360

AACTATCGCC GGCTGACCCG CTACACTGGG TCCA ATG ACC GGA CTA TCG CGA        412
                                       Met Thr Gly Leu Ser Arg
                                        1               5

CGC AAC GTT CTG ATC GGT TCG CTC GTG GCG GCA GCT GCC GTC GGT GCC      460
Arg Asn Val Leu Ile Gly Ser Leu Val Ala Ala Ala Ala Val Gly Ala
         10                  15                  20

GGC GTC GGT GGC GCC GCA CCG GCA TTC GCG GCA CCG ATC GAT GAC CAG      508
Gly Val Gly Gly Ala Ala Pro Ala Phe Ala Ala Pro Ile Asp Asp Gln
     25                  30                  35

CTG GCG GAA CTG GAG CGT CGG GAC AAC GTC CTG ATC GGC TTG TAC GCA      556
Leu Ala Glu Leu Glu Arg Arg Asp Asn Val Leu Ile Gly Leu Tyr Ala
     40                  45                  50

GCC AAT CTG CAG TCT GGG CGG AGG ATC ACG CAC CGT CCC GAC GAG ATG      604
Ala Asn Leu Gln Ser Gly Arg Arg Ile Thr His Arg Pro Asp Glu Met
 55                  60                  65                  70

TTC GCG ATG TGC TCG ACG TTC AAG GGC TAC GTC GGC TGC GGG GTG CTG      652
Phe Ala Met Cys Ser Thr Phe Lys Gly Tyr Val Gly Cys Gly Val Leu
                 75                  80                  85

CAG ATG GCC GAG CAC GGC GAG ATC TCA CTG GAC AAC CGG GTC TTC GTC      700
```

```
Gln  Met  Ala  Glu  His  Gly  Glu  Ile  Ser  Leu  Asp  Asn  Arg  Val  Phe  Val
               90                  95                       100
```

| GAT | GCG | GAT | GCG | CTC | GTG | CCG | AAC | TCA | CCC | GTC | ACC | GAG | ACA | CGT | GCC | 748 |
|---|---|---|---|---|---|---|---|---|---|---|---|---|---|---|---|---|
| Asp | Ala | Asp | Ala | Leu | Val | Pro | Asn | Ser | Pro | Val | Thr | Glu | Thr | Arg | Ala | |
| | | 105 | | | | | 110 | | | | | 115 | | | | |

| GGT | GCC | GAG | ATG | ACG | TTG | GCC | GAG | CTG | TGC | CAG | GCG | GCG | CTG | CAG | CGC | 796 |
|---|---|---|---|---|---|---|---|---|---|---|---|---|---|---|---|---|
| Gly | Ala | Glu | Met | Thr | Leu | Ala | Glu | Leu | Cys | Gln | Ala | Ala | Leu | Gln | Arg | |
| | 120 | | | | | 125 | | | | | 130 | | | | | |

| AGT | GAC | AAC | ACC | GCG | GCG | AAC | TTG | CTG | CTG | AAG | ACC | ATT | GGC | GGG | CCT | 844 |
|---|---|---|---|---|---|---|---|---|---|---|---|---|---|---|---|---|
| Ser | Asp | Asn | Thr | Ala | Ala | Asn | Leu | Leu | Leu | Lys | Thr | Ile | Gly | Gly | Pro | |
| 135 | | | | | 140 | | | | | 145 | | | | | 150 | |

| GCG | GCT | GTC | ACC | GCC | TTC | GCC | CGC | AGC | GTC | GGC | GAT | GAG | CGC | ACC | CGC | 892 |
|---|---|---|---|---|---|---|---|---|---|---|---|---|---|---|---|---|
| Ala | Ala | Val | Thr | Ala | Phe | Ala | Arg | Ser | Val | Gly | Asp | Glu | Arg | Thr | Arg | |
| | | | | 155 | | | | | 160 | | | | | 165 | | |

| CTG | GAC | CGC | TGG | GAG | GTA | GAG | CTG | AAC | TCC | GCG | ATA | CCC | GGG | GAC | CCG | 940 |
|---|---|---|---|---|---|---|---|---|---|---|---|---|---|---|---|---|
| Leu | Asp | Arg | Trp | Glu | Val | Glu | Leu | Asn | Ser | Ala | Ile | Pro | Gly | Asp | Pro | |
| | | | 170 | | | | | 175 | | | | | 180 | | | |

| AGG | GAC | ACC | AGC | ACG | CCG | GCG | GGC | CTG | GCG | GTC | GGA | TAC | CGC | GCG | ATT | 988 |
|---|---|---|---|---|---|---|---|---|---|---|---|---|---|---|---|---|
| Arg | Asp | Thr | Ser | Thr | Pro | Ala | Gly | Leu | Ala | Val | Gly | Tyr | Arg | Ala | Ile | |
| | | 185 | | | | | 190 | | | | | 195 | | | | |

| CTG | GCC | GGT | GAC | GCA | CTG | AGC | CCG | CCG | CAG | CGC | GCC | TGT | TGG | AAG | ACT | 1036 |
|---|---|---|---|---|---|---|---|---|---|---|---|---|---|---|---|---|
| Leu | Ala | Gly | Asp | Ala | Leu | Ser | Pro | Pro | Gln | Arg | Ala | Cys | Trp | Lys | Thr | |
| | 200 | | | | | 205 | | | | | 210 | | | | | |

| GGA | TGC | GGG | CCA | ATC | GAG | CCT | CGA | GCA | TGC | GTG | CCG | GGC | TTC | CCG | GAG | 1084 |
|---|---|---|---|---|---|---|---|---|---|---|---|---|---|---|---|---|
| Gly | Cys | Gly | Pro | Ile | Glu | Pro | Arg | Ala | Cys | Val | Pro | Gly | Phe | Pro | Glu | |
| 215 | | | | | 220 | | | | | 225 | | | | | 230 | |

| GGC | TGG | ACC | ACC | GCG | GAC | AAA | ACC | GGC | AGC | GGC | GAT | TAC | GGC | AGC | ACC | 1132 |
|---|---|---|---|---|---|---|---|---|---|---|---|---|---|---|---|---|
| Gly | Trp | Thr | Thr | Ala | Asp | Lys | Thr | Gly | Ser | Gly | Asp | Tyr | Gly | Ser | Thr | |
| | | | | 235 | | | | | 240 | | | | | 245 | | |

| AAC | GAC | GCC | GGA | ATC | GCT | TTC | GGA | CCC | GAC | GGA | CAA | CGG | TTG | CTG | TTG | 1180 |
|---|---|---|---|---|---|---|---|---|---|---|---|---|---|---|---|---|
| Asn | Asp | Ala | Gly | Ile | Ala | Phe | Gly | Pro | Asp | Gly | Gln | Arg | Leu | Leu | Leu | |
| | | | 250 | | | | | 255 | | | | | 260 | | | |

| GTG | ATG | ATG | ACG | CGA | TCG | CAG | GCC | CAT | GAC | CCC | AAG | GCC | GAG | AAC | CTG | 1228 |
|---|---|---|---|---|---|---|---|---|---|---|---|---|---|---|---|---|
| Val | Met | Met | Thr | Arg | Ser | Gln | Ala | His | Asp | Pro | Lys | Ala | Glu | Asn | Leu | |
| | | 265 | | | | | 270 | | | | | 275 | | | | |

| CGA | CCG | CTC | ATC | GGT | GAG | CTG | ACG | GCG | CTG | GTG | CTG | CCG | TCC | TTA | CTC | 1276 |
|---|---|---|---|---|---|---|---|---|---|---|---|---|---|---|---|---|
| Arg | Pro | Leu | Ile | Gly | Glu | Leu | Thr | Ala | Leu | Val | Leu | Pro | Ser | Leu | Leu | |
| | 280 | | | | | 285 | | | | | 290 | | | | | |

| TGAGTGCTCG | ACGGATTCGA | TTGCCGTCGA | ACCGTTTTCG | GTGCTCTGGA | TCGCGATCTG | 1336 |
| GCGGCTCCGG | CGGGGTTCTG | TGTCAACGGC | ACACGTACGG | TCAGGATGCC | GCGGTCGTAG | 1396 |
| CCGGCGGTGA | TGTTGTCCTC | GTCCGCCTCG | | | | 1426 |

( 2 ) INFORMATION FOR SEQ ID NO:3:

( i ) SEQUENCE CHARACTERISTICS:
        ( A ) LENGTH: 294 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Thr  Gly  Leu  Ser  Arg  Arg  Asn  Val  Leu  Ile  Gly  Ser  Leu  Val  Ala
 1              5                   10                      15

Ala  Ala  Ala  Val  Gly  Ala  Gly  Val  Gly  Gly  Ala  Ala  Pro  Ala  Phe  Ala
               20                  25                      30

Ala  Pro  Ile  Asp  Asp  Gln  Leu  Ala  Glu  Leu  Glu  Arg  Arg  Asp  Asn  Val
               35                  40                      45

Leu  Ile  Gly  Leu  Tyr  Ala  Ala  Asn  Leu  Gln  Ser  Gly  Arg  Arg  Ile  Thr
               50                  55                      60
```

```
His  Arg  Pro  Asp  Glu  Met  Phe  Ala  Met  Cys  Ser  Thr  Phe  Lys  Gly  Tyr
 65                  70                  75                  80

Val  Gly  Cys  Gly  Val  Leu  Gln  Met  Ala  Glu  His  Gly  Glu  Ile  Ser  Leu
                85                  90                       95

Asp  Asn  Arg  Val  Phe  Val  Asp  Ala  Asp  Ala  Leu  Val  Pro  Asn  Ser  Pro
               100                 105                      110

Val  Thr  Glu  Thr  Arg  Ala  Gly  Ala  Glu  Met  Thr  Leu  Ala  Glu  Leu  Cys
          115                      120                      125

Gln  Ala  Ala  Leu  Gln  Arg  Ser  Asp  Asn  Thr  Ala  Ala  Asn  Leu  Leu  Leu
     130                      135                 140

Lys  Thr  Ile  Gly  Gly  Pro  Ala  Ala  Val  Thr  Ala  Phe  Ala  Arg  Ser  Val
145                      150                 155                           160

Gly  Asp  Glu  Arg  Thr  Arg  Leu  Asp  Arg  Trp  Glu  Val  Glu  Leu  Asn  Ser
               165                      170                      175

Ala  Ile  Pro  Gly  Asp  Pro  Arg  Asp  Thr  Ser  Thr  Pro  Ala  Gly  Leu  Ala
               180                 185                      190

Val  Gly  Tyr  Arg  Ala  Ile  Leu  Ala  Gly  Asp  Ala  Leu  Ser  Pro  Pro  Gln
          195                 200                      205

Arg  Ala  Cys  Trp  Lys  Thr  Gly  Cys  Gly  Pro  Ile  Glu  Pro  Arg  Ala  Cys
     210                      215                 220

Val  Pro  Gly  Phe  Pro  Glu  Gly  Trp  Thr  Thr  Ala  Asp  Lys  Thr  Gly  Ser
225                 230                      235                           240

Gly  Asp  Tyr  Gly  Ser  Thr  Asn  Asp  Ala  Gly  Ile  Ala  Phe  Gly  Pro  Asp
               245                      250                      255

Gly  Gln  Arg  Leu  Leu  Leu  Val  Met  Met  Thr  Arg  Ser  Gln  Ala  His  Asp
          260                      265                      270

Pro  Lys  Ala  Glu  Asn  Leu  Arg  Pro  Leu  Ile  Gly  Glu  Leu  Thr  Ala  Leu
          275                      280                      285

Val  Leu  Pro  Ser  Leu  Leu
          290
```

( 2 ) INFORMATION FOR SEQ ID NO:4:

( i ) SEQUENCE CHARACTERISTICS:
        ( A ) LENGTH: 293 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Region
        ( B ) LOCATION: 39..46

( i x ) FEATURE:
        ( A ) NAME/KEY: Region
        ( B ) LOCATION: 49..56

( i x ) FEATURE:
        ( A ) NAME/KEY: Region
        ( B ) LOCATION: 60..65

( i x ) FEATURE:
        ( A ) NAME/KEY: Region
        ( B ) LOCATION: 66..75

( i x ) FEATURE:
        ( A ) NAME/KEY: Region
        ( B ) LOCATION: 76..87

( i x ) FEATURE:
        ( A ) NAME/KEY: Region
        ( B ) LOCATION: 88..111

( i x ) FEATURE:
    ( A ) NAME/KEY: Region
    ( B ) LOCATION: 112..118

( i x ) FEATURE:
    ( A ) NAME/KEY: Region
    ( B ) LOCATION: 119..124

( i x ) FEATURE:
    ( A ) NAME/KEY: Region
    ( B ) LOCATION: 125..132

( i x ) FEATURE:
    ( A ) NAME/KEY: Region
    ( B ) LOCATION: 137..147

( i x ) FEATURE:
    ( A ) NAME/KEY: Region
    ( B ) LOCATION: 150..160

( i x ) FEATURE:
    ( A ) NAME/KEY: Region
    ( B ) LOCATION: 171..176

( i x ) FEATURE:
    ( A ) NAME/KEY: Region
    ( B ) LOCATION: 188..198

( i x ) FEATURE:
    ( A ) NAME/KEY: Region
    ( B ) LOCATION: 208..215

( i x ) FEATURE:
    ( A ) NAME/KEY: Region
    ( B ) LOCATION: 220..227

( i x ) FEATURE:
    ( A ) NAME/KEY: Region
    ( B ) LOCATION: 232..240

( i x ) FEATURE:
    ( A ) NAME/KEY: Region
    ( B ) LOCATION: 243..253

( i x ) FEATURE:
    ( A ) NAME/KEY: Region
    ( B ) LOCATION: 254..258

( i x ) FEATURE:
    ( A ) NAME/KEY: Region
    ( B ) LOCATION: 259..269

( i x ) FEATURE:
    ( A ) NAME/KEY: Region
    ( B ) LOCATION: 280..293

( x i ) SEQUENCE DESCRIPTION: SEQ ID NO:4:

```
Met  Thr  Gly  Leu  Ser  Arg  Arg  Asn  Val  Leu  Ile  Gly  Ser  Leu  Val  Ala
 1              5                        10                       15

Ala  Ala  Ala  Val  Gly  Ala  Gly  Val  Gly  Gly  Ala  Ala  Pro  Ala  Phe  Ala
               20                       25                       30

Ala  Pro  Ile  Asp  Asp  Gln  Leu  Ala  Glu  Leu  Glu  Arg  Arg  Asp  Asn  Val
          35                       40                       45

Leu  Ile  Gly  Leu  Tyr  Ala  Ala  Asn  Leu  Gln  Ser  Gly  Arg  Arg  Ile  Thr
     50                       55                       60

His  Arg  Pro  Asp  Glu  Met  Phe  Ala  Met  Cys  Ser  Thr  Phe  Lys  Gly  Tyr
65                       70                       75                       80

Val  Ala  Ala  Arg  Val  Leu  Gln  Met  Ala  Glu  His  Gly  Glu  Ile  Ser  Leu
               85                       90                       95

Asp  Asn  Arg  Val  Phe  Val  Asp  Ala  Asp  Ala  Leu  Val  Pro  Asn  Ser  Pro
              100                      105                      110
```

```
Val  Thr  Glu  Thr  Arg  Ala  Gly  Ala  Glu  Met  Thr  Leu  Ala  Glu  Leu  Cys
          115                 120                      125

Gln  Ala  Ala  Leu  Gln  Arg  Ser  Asp  Asn  Thr  Ala  Ala  Asn  Leu  Leu  Leu
     130                 135                      140

Lys  Thr  Ile  Gly  Gly  Pro  Ala  Ala  Val  Thr  Ala  Phe  Ala  Arg  Ser  Val
145                      150                      155                           160

Gly  Asp  Glu  Arg  Thr  Arg  Leu  Asp  Arg  Trp  Glu  Val  Glu  Leu  Asn  Ser
               165                      170                           175

Ala  Ile  Pro  Gly  Asp  Pro  Arg  Asp  Thr  Ser  Thr  Pro  Ala  Gly  Leu  Ala
               180                 185                      190

Val  Gly  Tyr  Arg  Ala  Ile  Leu  Ala  Gly  Asp  Ala  Leu  Ser  Pro  Pro  Gln
          195                 200                      205

Arg  Ala  Cys  Trp  Lys  Thr  Gly  Cys  Gly  Pro  Ile  Glu  Pro  Arg  Ala  Cys
     210                 215                      220

Val  Pro  Gly  Pro  Glu  Gly  Trp  Thr  Thr  Ala  Asp  Lys  Thr  Gly  Ser  Gly
225                      230                 235                           240

Asp  Tyr  Gly  Ser  Thr  Asn  Asp  Ala  Gly  Ile  Ala  Phe  Gly  Pro  Asp  Gly
               245                      250                      255

Gln  Arg  Leu  Leu  Leu  Val  Met  Met  Thr  Arg  Ser  Gln  Ala  His  Asp  Pro
               260                 265                      270

Lys  Ala  Glu  Asn  Leu  Arg  Pro  Leu  Ile  Gly  Glu  Leu  Thr  Ala  Leu  Val
     275                      280                      285

Leu  Pro  Ser  Leu  Leu
     290
```

( 2 ) INFORMATION FOR SEQ ID NO:5:

( i ) SEQUENCE CHARACTERISTICS:
        ( A ) LENGTH: 313 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Val  His  Pro  Ser  Thr  Ser  Arg  Pro  Ser  Arg  Arg  Thr  Ile  Leu  Thr  Ala
1                   5                   10                       15

Thr  Ala  Gly  Ala  Ala  Leu  Ala  Ala  Thr  Leu  Val  Pro  Gly  Thr  Ala
               20                 25                      30

His  Ala  Ser  Ser  Gly  Gly  Arg  Gly  His  Gly  Ser  Gly  Ser  Val  Ser  Asp
          35                 40                      45

Ala  Glu  Arg  Arg  Leu  Ala  Gly  Leu  Glu  Arg  Ala  Ser  Gly  Ala  Arg  Leu
     50                      55                      60

Gly  Val  Tyr  Ala  Tyr  Asp  Thr  Gly  Ser  Gly  Arg  Thr  Val  Ala  Tyr  Arg
65                       70                      75                            80

Ala  Asp  Glu  Leu  Phe  Pro  Met  Cys  Ser  Val  Phe  Lys  Thr  Leu  Ser  Ser
               85                      90                           95

Ala  Ala  Val  Leu  Arg  Asp  Leu  Asp  Arg  Asn  Gly  Glu  Phe  Leu  Ser  Arg
               100                     105                     110

Arg  Ile  Leu  Tyr  Thr  Gln  Asp  Asp  Val  Glu  Gln  Ala  Asp  Gly  Ala  Gly
          115                     120                     125

Pro  Glu  Thr  Gly  Lys  Pro  Gln  Asn  Leu  Ala  Asn  Ala  Gln  Leu  Thr  Val
     130                     135                     140

Glu  Glu  Leu  Cys  Glu  Val  Ser  Ile  Thr  Ala  Ser  Asp  Asn  Cys  Ala  Ala
145                     150                     155                           160

Asn  Leu  Met  Leu  Arg  Glu  Leu  Gly  Gly  Pro  Ala  Ala  Val  Thr  Arg  Phe
```

|     |     |     |     |     |     | 165 |     |     |     |     |     | 170 |     |     |     |     |     | 175 |     |
| --- | --- | --- | --- | --- | --- | --- | --- | --- | --- | --- | --- | --- | --- | --- | --- | --- | --- | --- | --- |
| Val | Arg | Ser | Leu<br>180 | Gly | Asp | Arg | Val | Thr<br>185 | Arg | Leu | Asp | Arg | Trp<br>190 | Glu | Pro |
| Glu | Leu | Asn<br>195 | Ser | Ala | Glu | Pro | Gly<br>200 | Arg | Val | Thr | Asp | Thr<br>205 | Thr | Ser | Pro |
| Arg | Ala<br>210 | Ile | Thr | Arg | Thr | Tyr<br>215 | Gly | Arg | Leu | Val | Leu<br>220 | Gly | Asp | Ala | Leu |
| Asn<br>225 | Pro | Arg | Asp | Arg | Ala<br>230 | Leu | Leu | Thr | Ser | Trp<br>235 | Leu | Leu | Ala | Asn | Thr<br>240 |
| Thr | Ser | Gly | Asp | Arg<br>245 | Phe | Arg | Ala | Gly | Leu<br>250 | Pro | Asp | Asp | Trp | Thr<br>255 | Leu |
| Gly | Asp | Lys | Thr<br>260 | Gly | Ala | Gly | Arg | Tyr<br>265 | Gly | Thr | Asn | Asp | Ala<br>270 | Gly | Val |
| Thr | Trp | Pro<br>275 | Pro | Gly | Arg | Ala | Pro<br>280 | Ile | Val | Leu | Thr | Val<br>285 | Leu | Thr | Ala |
| Lys | Thr<br>290 | Glu | Gln | Asp | Ala | Ala<br>295 | Arg | Asp | Asp | Gly | Leu<br>300 | Val | Ala | Asp | Ala |
| Ala<br>305 | Arg | Val | Leu | Ala | Glu<br>310 | Thr | Leu | Gly |

( 2 ) INFORMATION FOR SEQ ID NO:6:

( i ) SEQUENCE CHARACTERISTICS:
        ( A ) LENGTH: 281 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Region
        ( B ) LOCATION: 27..34

( i x ) FEATURE:
        ( A ) NAME/KEY: Region
        ( B ) LOCATION: 37..44

( i x ) FEATURE:
        ( A ) NAME/KEY: Region
        ( B ) LOCATION: 48..53

( i x ) FEATURE:
        ( A ) NAME/KEY: Region
        ( B ) LOCATION: 64..75

( i x ) FEATURE:
        ( A ) NAME/KEY: Region
        ( B ) LOCATION: 98..104

( i x ) FEATURE:
        ( A ) NAME/KEY: Region
        ( B ) LOCATION: 111..118

( i x ) FEATURE:
        ( A ) NAME/KEY: Region
        ( B ) LOCATION: 123..133

( i x ) FEATURE:
        ( A ) NAME/KEY: Region
        ( B ) LOCATION: 136..146

( i x ) FEATURE:
        ( A ) NAME/KEY: Region
        ( B ) LOCATION: 157..162

( i x ) FEATURE:
        ( A ) NAME/KEY: Region
        ( B ) LOCATION: 174..184

( i x ) FEATURE:
    ( A ) NAME/KEY: Region
    ( B ) LOCATION: 192..204

( i x ) FEATURE:
    ( A ) NAME/KEY: Region
    ( B ) LOCATION: 209..216

( i x ) FEATURE:
    ( A ) NAME/KEY: Region
    ( B ) LOCATION: 221..229

( i x ) FEATURE:
    ( A ) NAME/KEY: Region
    ( B ) LOCATION: 233..243

( i x ) FEATURE:
    ( A ) NAME/KEY: Region
    ( B ) LOCATION: 249..259

( i x ) FEATURE:
    ( A ) NAME/KEY: Region
    ( B ) LOCATION: 269..281

( x i ) SEQUENCE DESCRIPTION: SEQ ID NO:6:

```
Met Lys Lys Leu Ile Phe Leu Ile Val Ile Ala Leu Val Leu Ser Ala
 1               5                  10                  15

Cys Asn Ser Asn Ser Ser His Ala Lys Glu Leu Asn Asp Leu Glu Lys
             20                  25                  30

Lys Tyr Asn Ala His Ile Gly Val Tyr Ala Leu Asp Thr Lys Ser Gly
         35                  40                  45

Lys Glu Val Lys Phe Asn Ser Asp Lys Arg Phe Ala Tyr Ala Ser Thr
     50                  55                  60

Ser Lys Ala Ile Asn Ser Ala Ile Leu Leu Glu Gln Val Pro Tyr Asn
 65                  70                  75                  80

Lys Leu Asn Lys Lys Val His Ile Asn Lys Asp Asp Ile Val Ala Tyr
                 85                  90                  95

Ser Pro Ile Leu Glu Lys Tyr Val Gly Lys Asp Ile Thr Leu Lys Ala
                100                 105                 110

Leu Ile Glu Ala Ser Met Thr Tyr Ser Asp Asn Thr Ala Asn Asn Lys
            115                 120                 125

Ile Ile Lys Glu Ile Gly Gly Ile Lys Lys Val Lys Gln Arg Leu Lys
        130                 135                 140

Glu Leu Gly Asp Lys Val Thr Asn Pro Val Arg Tyr Glu Ile Glu Leu
145                 150                 155                 160

Asn Tyr Tyr Ser Pro Lys Ser Lys Lys Asp Thr Ser Thr Pro Ala Ala
                165                 170                 175

Phe Gly Lys Thr Leu Asn Lys Leu Ile Ala Asn Gly Lys Leu Ser Lys
                180                 185                 190

Glu Asn Lys Lys Phe Leu Leu Asp Leu Met Leu Asn Asn Lys Ser Gly
            195                 200                 205

Asp Thr Leu Ile Lys Asp Gly Val Pro Lys Asp Tyr Lys Val Ala Asp
        210                 215                 220

Lys Ser Gly Gln Ala Ile Thr Tyr Ala Ser Arg Asn Asp Val Ala Phe
225                 230                 235                 240

Val Tyr Pro Lys Gly Gln Ser Glu Pro Ile Val Leu Val Ile Phe Thr
                245                 250                 255

Asn Lys Asp Asn Lys Ser Asp Lys Pro Asn Asp Lys Leu Ile Ser Glu
            260                 265                 270

Thr Ala Lys Ser Val Met Lys Glu Phe
        275                 280
```

( 2 ) INFORMATION FOR SEQ ID NO:7:

( i ) SEQUENCE CHARACTERISTICS:
        ( A ) LENGTH: 1426 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 395..1276

( i x ) FEATURE:
        ( A ) NAME/KEY: misc_feature
        ( B ) LOCATION: 563..568

( i x ) FEATURE:
        ( A ) NAME/KEY: misc_feature
        ( B ) LOCATION: 672..677

( i x ) FEATURE:
        ( A ) NAME/KEY: misc_feature
        ( B ) LOCATION: 506..532

( i x ) FEATURE:
        ( A ) NAME/KEY: misc_feature
        ( B ) LOCATION: 539..562

( i x ) FEATURE:
        ( A ) NAME/KEY: misc_feature
        ( B ) LOCATION: 572..589

( i x ) FEATURE:
        ( A ) NAME/KEY: misc_feature
        ( B ) LOCATION: 620..652

( i x ) FEATURE:
        ( A ) NAME/KEY: misc_feature
        ( B ) LOCATION: 725..748

( i x ) FEATURE:
        ( A ) NAME/KEY: misc_feature
        ( B ) LOCATION: 764..790

( i x ) FEATURE:
        ( A ) NAME/KEY: misc_feature
        ( B ) LOCATION: 815..835

( i x ) FEATURE:
        ( A ) NAME/KEY: misc_feature
        ( B ) LOCATION: 842..874

( i x ) FEATURE:
        ( A ) NAME/KEY: misc_feature
        ( B ) LOCATION: 905..925

( i x ) FEATURE:
        ( A ) NAME/KEY: misc_feature
        ( B ) LOCATION: 956..988

( i x ) FEATURE:
        ( A ) NAME/KEY: misc_feature
        ( B ) LOCATION: 1016..1036

( i x ) FEATURE:
        ( A ) NAME/KEY: misc_feature
        ( B ) LOCATION: 1052..1075

( i x ) FEATURE:
        ( A ) NAME/KEY: misc_feature
        ( B ) LOCATION: 1061..1066

( i x ) FEATURE:
        ( A ) NAME/KEY: misc_feature
        ( B ) LOCATION: 1091..1117

( i x ) FEATURE:

(A) NAME/KEY: misc_feature
(B) LOCATION: 1127..1156

(ix) FEATURE:
(A) NAME/KEY: misc_feature
(B) LOCATION: 1172..1204

(ix) FEATURE:
(A) NAME/KEY: misc_feature
(B) LOCATION: 1235..1276

(xi) SEQUENCE DESCRIPTION: SEQ ID NO:7:

```
CTCTGTCGTG TATGCGGATG TCAGCCGGAA CGTTCGACAA AGTGGTGCGG GTGACCACCG        60

AAGTTTTGGA AGGTGTTGCC AGAAGACGGG TCACCGCCGA CGAATGCCGG ATCCGCAAAG       120

GCTCGTTGCG CGGTGGGCTG GTGCTCGGCC TGGAGGATTC CGGATCACGT AAGCACCGGA       180

TCGGCCGTAG CGAGCTCAAT TACGGTGAGC ACCGGACCAT CGACCACACG CTGCTGGCCC       240

AGATCGAGGC AGTCACTCTA GAAGAGGTCA ACGCCGTCGC TCACCAGTTC GTGTCGCGGG       300

ACTACGGTGC CGCCGTACTC GGTCCCTATA GTTCGAAAAA GCGCTGCCAC AACAGCTTCA       360

AACTATCGCC GGCTGACCCG CTACACTGGG TCCA ATG ACC GGA CTA TCG CGA          412
                                     Met Thr Gly Leu Ser Arg
                                     295               300
```

| | | | | | | | | | | | | | | | | |
|---|---|---|---|---|---|---|---|---|---|---|---|---|---|---|---|---|
| CGC | AAC | GTT | CTG | ATC | GGT | TCG | CTC | GTG | GCG | GCA | GCT | GCC | GTC | GGT | GCC | 460 |
| Arg | Asn | Val | Leu | Ile | Gly | Ser | Leu | Val | Ala | Ala | Ala | Ala | Val | Gly | Ala | |
| | | | | 305 | | | | 310 | | | | | 315 | | | |
| GGC | GTC | GGT | GGC | GCC | GCA | CCG | GCA | TTC | GCG | GCA | CCG | ATC | GAT | GAC | CAG | 508 |
| Gly | Val | Gly | Gly | Ala | Ala | Pro | Ala | Phe | Ala | Ala | Pro | Ile | Asp | Asp | Gln | |
| | | | 320 | | | | | 325 | | | | | 330 | | | |
| CTG | GCG | GAA | CTG | GAG | CGT | CGG | GAC | AAC | GTC | CTG | ATC | GGC | TTG | TAC | GCA | 556 |
| Leu | Ala | Glu | Leu | Glu | Arg | Arg | Asp | Asn | Val | Leu | Ile | Gly | Leu | Tyr | Ala | |
| | | 335 | | | | | 340 | | | | | 345 | | | | |
| GCC | AAT | CTG | CAG | TCT | GGG | CGG | AGG | ATC | ACG | CAC | CGT | CCC | GAC | GAG | ATG | 604 |
| Ala | Asn | Leu | Gln | Ser | Gly | Arg | Arg | Ile | Thr | His | Arg | Pro | Asp | Glu | Met | |
| | 350 | | | | | 355 | | | | | 360 | | | | | |
| TTC | GCG | ATG | TGC | TCG | ACG | TTC | AAG | GGC | TAC | GTC | GGC | TGC | GGG | GTG | CTG | 652 |
| Phe | Ala | Met | Cys | Ser | Thr | Phe | Lys | Gly | Tyr | Val | Gly | Cys | Gly | Val | Leu | |
| 365 | | | | | 370 | | | | | 375 | | | | | 380 | |
| CAG | ATG | GCC | GAG | CAC | GGC | GAG | ATC | TCA | CTG | GAC | AAC | CGG | GTC | TTC | GTC | 700 |
| Gln | Met | Ala | Glu | His | Gly | Glu | Ile | Ser | Leu | Asp | Asn | Arg | Val | Phe | Val | |
| | | | | 385 | | | | | 390 | | | | | 395 | | |
| GAT | GCG | GAT | GCG | CTC | GTG | CCG | AAC | TCA | CCC | GTC | ACC | GAG | ACA | CGT | GCC | 748 |
| Asp | Ala | Asp | Ala | Leu | Val | Pro | Asn | Ser | Pro | Val | Thr | Glu | Thr | Arg | Ala | |
| | | | 400 | | | | | 405 | | | | | 410 | | | |
| GGT | GCC | GAG | ATG | ACG | TTG | GCC | GAG | CTG | TGC | CAG | GCG | GCG | CTG | CAG | CGC | 796 |
| Gly | Ala | Glu | Met | Thr | Leu | Ala | Glu | Leu | Cys | Gln | Ala | Ala | Leu | Gln | Arg | |
| | | | 415 | | | | | 420 | | | | | 425 | | | |
| AGT | GAC | AAC | ACC | GCG | GCG | AAC | TTG | CTG | CTG | AAG | ACC | ATT | GGC | GGG | CCT | 844 |
| Ser | Asp | Asn | Thr | Ala | Ala | Asn | Leu | Leu | Leu | Lys | Thr | Ile | Gly | Gly | Pro | |
| | 430 | | | | | 435 | | | | | 440 | | | | | |
| GCG | GCT | GTC | ACC | GCC | TTC | GCC | CGC | AGC | GTC | GGC | GAT | GAG | CGC | ACC | CGC | 892 |
| Ala | Ala | Val | Thr | Ala | Phe | Ala | Arg | Ser | Val | Gly | Asp | Glu | Arg | Thr | Arg | |
| 445 | | | | | 450 | | | | | 455 | | | | | 460 | |
| CTG | GAC | CGC | TGG | GAG | GTA | GAG | CTG | AAC | TCC | GCG | ATA | CCC | GGG | GAC | CCG | 940 |
| Leu | Asp | Arg | Trp | Glu | Val | Glu | Leu | Asn | Ser | Ala | Ile | Pro | Gly | Asp | Pro | |
| | | | | 465 | | | | | 470 | | | | | 475 | | |
| AGG | GAC | ACC | AGC | ACG | CCG | GCG | GGC | CTG | GCG | GTC | GGA | TAC | CGC | GCG | ATT | 988 |
| Arg | Asp | Thr | Ser | Thr | Pro | Ala | Gly | Leu | Ala | Val | Gly | Tyr | Arg | Ala | Ile | |
| | | | 480 | | | | | 485 | | | | | 490 | | | |
| CTG | GCC | GGT | GAC | GCA | CTG | AGC | CCG | CCG | CAG | CGC | GCC | TGT | TGG | AAG | ACT | 1036 |
| Leu | Ala | Gly | Asp | Ala | Leu | Ser | Pro | Pro | Gln | Arg | Ala | Cys | Trp | Lys | Thr | |
| | | 495 | | | | | 500 | | | | | 505 | | | | |

| | | | | | | | | | | | | | | | | |
|---|---|---|---|---|---|---|---|---|---|---|---|---|---|---|---|---|
|GGA|TGC|GGG|CCA|ATC|GAG|CCT|CGA|GCA|TGC|GTG|CCG|GGC|TTC|CCG|GAG|1084|
|Gly|Cys|Gly|Pro|Ile|Glu|Pro|Arg|Ala|Cys|Val|Pro|Gly|Phe|Pro|Glu||
| |510| | | |515| | | | |520| | | | | | |
|GGC|TGG|ACC|ACC|GCG|GAC|AAA|ACC|GGC|AGC|GGC|GAT|TAC|GGC|AGC|ACC|1132|
|Gly|Trp|Thr|Thr|Ala|Asp|Lys|Thr|Gly|Ser|Gly|Asp|Tyr|Gly|Ser|Thr||
|525| | | | |530| | | | |535| | | | |540| |
|AAC|GAC|GCC|GGA|ATC|GCT|TTC|GGA|CCC|GAC|GGA|CAA|CGG|TTG|CTG|TTG|1180|
|Asn|Asp|Ala|Gly|Ile|Ala|Phe|Gly|Pro|Asp|Gly|Gln|Arg|Leu|Leu|Leu||
| | | | |545| | | | |550| | | | |555| | |
|GTG|ATG|ATG|ACG|CGA|TCG|CAG|GCC|CAT|GAC|CCC|AAG|GCC|GAG|AAC|CTG|1228|
|Val|Met|Met|Thr|Arg|Ser|Gln|Ala|His|Asp|Pro|Lys|Ala|Glu|Asn|Leu||
| | | |560| | | | |565| | | | |570| | | |
|CGA|CCG|CTC|ATC|GGT|GAG|CTG|ACG|GCG|CTG|GTG|CTG|CCG|TCC|TTA|CTC|1276|
|Arg|Pro|Leu|Ile|Gly|Glu|Leu|Thr|Ala|Leu|Val|Leu|Pro|Ser|Leu|Leu||
| | |575| | | | |580| | | | |585| | | | |

TGAGTGCTCG ACGGATTCGA TTGCCGTCGA ACCGTTTTCG GTGCTCTGGA TCGCGATCTG    1336

GCGGCTCCGG CGGGGTTCTG TGTCAACGGC ACACGTACGG TCAGGATGCC GCGGTCGTAG    1396

CCGGCGGTGA TGTTGTCCTC GTCCGCCTCG    1426

( 2 ) INFORMATION FOR SEQ ID NO:8:

( i ) SEQUENCE CHARACTERISTICS:
        ( A ) LENGTH: 294 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | | |
|---|---|---|---|---|---|---|---|---|---|---|---|---|---|---|---|
|Met|Thr|Gly|Leu|Ser|Arg|Arg|Asn|Val|Leu|Ile|Gly|Ser|Leu|Val|Ala|
|1| | | |5| | | |10| | | | |15| | |
|Ala|Ala|Ala|Val|Gly|Ala|Gly|Val|Gly|Gly|Ala|Ala|Pro|Ala|Phe|Ala|
| | | | |20| | | |25| | | | |30| | |
|Ala|Pro|Ile|Asp|Asp|Gln|Leu|Ala|Glu|Leu|Glu|Arg|Arg|Asp|Asn|Val|
| | | |35| | | | |40| | | |45| | | |
|Leu|Ile|Gly|Leu|Tyr|Ala|Ala|Asn|Leu|Gln|Ser|Gly|Arg|Arg|Ile|Thr|
| |50| | | | |55| | | | |60| | | | |
|His|Arg|Pro|Asp|Glu|Met|Phe|Ala|Met|Cys|Ser|Thr|Phe|Lys|Gly|Tyr|
|65| | | | |70| | | |75| | | | | |80|
|Val|Gly|Cys|Gly|Val|Leu|Gln|Met|Ala|Glu|His|Gly|Glu|Ile|Ser|Leu|
| | | | |85| | | |90| | | | |95| | |
|Asp|Asn|Arg|Val|Phe|Val|Asp|Ala|Asp|Ala|Leu|Val|Pro|Asn|Ser|Pro|
| | | |100| | | | |105| | | | |110| | |
|Val|Thr|Glu|Thr|Arg|Ala|Gly|Ala|Glu|Met|Thr|Leu|Ala|Glu|Leu|Cys|
| | |115| | | | |120| | | | |125| | | |
|Gln|Ala|Ala|Leu|Gln|Arg|Ser|Asp|Asn|Thr|Ala|Ala|Asn|Leu|Leu|Leu|
| |130| | | | |135| | | | |140| | | | |
|Lys|Thr|Ile|Gly|Gly|Pro|Ala|Ala|Val|Thr|Ala|Phe|Ala|Arg|Ser|Val|
|145| | | | |150| | | | |155| | | | |160|
|Gly|Asp|Glu|Arg|Thr|Arg|Leu|Asp|Arg|Trp|Glu|Val|Glu|Leu|Asn|Ser|
| | | | |165| | | | |170| | | | |175| |
|Ala|Ile|Pro|Gly|Asp|Pro|Arg|Asp|Thr|Ser|Thr|Pro|Ala|Gly|Leu|Ala|
| | | |180| | | | |185| | | | |190| | |
|Val|Gly|Tyr|Arg|Ala|Ile|Leu|Ala|Gly|Asp|Ala|Leu|Ser|Pro|Pro|Gln|
| | |195| | | | |200| | | | |205| | | |
|Arg|Ala|Cys|Trp|Lys|Thr|Gly|Cys|Gly|Pro|Ile|Glu|Pro|Arg|Ala|Cys|
| |210| | | | |215| | | | |220| | | | |

-continued

| Val | Pro | Gly | Phe | Pro | Glu | Gly | Trp | Thr | Thr | Ala | Asp | Lys | Thr | Gly | Ser |
|---|---|---|---|---|---|---|---|---|---|---|---|---|---|---|---|
| 225 | | | | | 230 | | | | | 235 | | | | | 240 |

| Gly | Asp | Tyr | Gly | Ser | Thr | Asn | Asp | Ala | Gly | Ile | Ala | Phe | Gly | Pro | Asp |
|---|---|---|---|---|---|---|---|---|---|---|---|---|---|---|---|
| | | | | 245 | | | | | 250 | | | | | 255 | |

| Gly | Gln | Arg | Leu | Leu | Leu | Val | Met | Met | Thr | Arg | Ser | Gln | Ala | His | Asp |
|---|---|---|---|---|---|---|---|---|---|---|---|---|---|---|---|
| | | | 260 | | | | | 265 | | | | | 270 | | |

| Pro | Lys | Ala | Glu | Asn | Leu | Arg | Pro | Leu | Ile | Gly | Glu | Leu | Thr | Ala | Leu |
|---|---|---|---|---|---|---|---|---|---|---|---|---|---|---|---|
| | | 275 | | | | | 280 | | | | | 285 | | | |

| Val | Leu | Pro | Ser | Leu | Leu |
|---|---|---|---|---|---|
| | | 290 | | | |

( 2 ) INFORMATION FOR SEQ ID NO:9:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

| Ala | Pro | Ile | Asp | Asp | Gln | Leu | Ala | Glu | Leu | Glu | Arg | Arg | Asp | Asn | Val |
|---|---|---|---|---|---|---|---|---|---|---|---|---|---|---|---|
| 1 | | | | 5 | | | | | 10 | | | | | 15 | |

| Leu | Ile | Gly | Leu | Tyr | Ala | Ala | Asn | Leu | Gln | Ser | Gly | Arg | Arg | Ile | Thr |
|---|---|---|---|---|---|---|---|---|---|---|---|---|---|---|---|
| | | | 20 | | | | | 25 | | | | | 30 | | |

| His | Arg | Pro | Asp | Glu | Met | Phe | Ala | Met | Xaa | Ser | Thr | Phe | Lys | Gly | Tyr |
|---|---|---|---|---|---|---|---|---|---|---|---|---|---|---|---|
| | | | 35 | | | | | 40 | | | | | 45 | | |

| Val |
|---|

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

| Ala | Pro | Ile | Asp | Asp | Gln |
|---|---|---|---|---|---|
| 1 | | | | 5 | |

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

GCSCCSATCG AYGAYCAG                                                18

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Ser  Thr  Phe  Lys  Gly  Tyr  Val
1                5
```

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

AGSTGSAAGT TCCCRATRCA S                                   21

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PRIMER"

( x i ) SEQUENCE DESCRIPTION: SEQ ID NO:14:

CTTGAAGGTC GAGCACATCG CGAACAT                        27

( 2 ) INFORMATION FOR SEQ ID NO:15:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PRIMER"

( x i ) SEQUENCE DESCRIPTION: SEQ ID NO:15:

ATTGGATCCT GGTACCCGAG GAGTGTACAA GACCCAACTA CAATAA      46

( 2 ) INFORMATION FOR SEQ ID NO:16:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "PRIMER"

( x i ) SEQUENCE DESCRIPTION: SEQ ID NO:16:

TTTGGATCCC TCTAGACCCG TCGCCACAAT GTGCTTGTCT TATAGTTCCT      50

( 2 ) INFORMATION FOR SEQ ID NO:17:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid (A) DESCRIPTION: /desc = "PRIMER"

(x i) SEQUENCE DESCRIPTION: SEQ ID NO:17:

AAACTGCAGG GATCCATGGG AAGTGACATA GCA             33

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "PRIMER"

(x i) SEQUENCE DESCRIPTION: SEQ ID NO:18:

CCCTGAAGCT TACTCGGCTC TTAGAGTTTT                30

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "PRIMER"

(x i) SEQUENCE DESCRIPTION: SEQ ID NO:19:

CGAATTCAGA TCTCAACTTT AAATGCATGG GTA             33

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "PRIMER"

(x i) SEQUENCE DESCRIPTION: SEQ ID NO:20:

GTTCGAATTC TCACAAACTC TTGC                       24

(2) INFORMATION FOR SEQ ID NO:21:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "PRIMER"

(x i) SEQUENCE DESCRIPTION: SEQ ID NO:21:

GCGGGATCCT TATGCATGTG CGCGACGTGA ACTGGGGC        38

(2) INFORMATION FOR SEQ ID NO:22:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: other nucleic acid (A) DESCRIPTION: /desc = "PRIMER"

(xi) SEQUENCE DESCRIPTION: SEQ ID NO:22:

CCGAATTCAA GCTTCTACGC CGTGTTGCCG CCGTCCTT 38